US011013508B2

(12) United States Patent
Arai et al.

(10) Patent No.: US 11,013,508 B2
(45) Date of Patent: May 25, 2021

(54) FENESTRATED LOCKING SUTURE ANCHOR ASSEMBLY

(71) Applicant: Smith & Nephew, Inc., Memphis, TN (US)

(72) Inventors: Tatsuya Arai, Franklin, MA (US); Matthew Edwin Koski, Westford, MA (US); Mark Edwin Housman, North Attleboro, MA (US); Richard M. Lunn, Kingston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 215 days.

(21) Appl. No.: 16/407,826

(22) Filed: May 9, 2019

(65) Prior Publication Data

US 2019/0261974 A1 Aug. 29, 2019

Related U.S. Application Data

(60) Continuation of application No. 15/346,980, filed on Nov. 9, 2016, now Pat. No. 10,335,137, which is a (Continued)

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); (Continued)

(58) Field of Classification Search
CPC ................... A61B 17/0401; A61B 2017/0409
See application file for complete search history.

(56) References Cited

U.S. PATENT DOCUMENTS

2008/0058816 A1* 3/2008 Philippon .......... A61B 17/8888
606/326
2010/0016869 A1* 1/2010 Paulk ................. A61B 17/0469
606/144
(Continued)

FOREIGN PATENT DOCUMENTS

WO WO-2011060022 A2 * 5/2011 ............ A61F 2/0811

OTHER PUBLICATIONS

Australian Examination Report No. 1—Application No. 2019202236 dated Aug. 16, 2019.
(Continued)

*Primary Examiner* — Tuan V Nguyen
(74) *Attorney, Agent, or Firm* — Burns & Levinson, LLP; Joseph M. Maraia

(57) ABSTRACT

The technology includes an anchor assembly for tissue repair having an open helical coil sleeve and a tip structure. The tip structure includes an aperture for passing a suture and a suture capture member for capturing a suture. The technology also includes an anchor driver for installing an anchor into bone. The anchor driver includes an outer shaft and a sleeve advancement member for advancing the sleeve as well as an inner shaft and a suture capture advancement member for advancing the suture capture member. The technology also includes a system for tissue repair having an anchor assembly and an anchor driver for installing the anchor assembly into bone.

20 Claims, 21 Drawing Sheets

Related U.S. Application Data division of application No. 13/838,729, filed on Mar. 15, 2013, now Pat. No. 9,526,488.

(52) U.S. Cl.
CPC .......... *A61B 2017/0414* (2013.01); *A61B 2017/0424* (2013.01); *A61B 2017/0438* (2013.01); *A61B 2017/0441* (2013.01); *A61B 2017/0445* (2013.01); *A61B 2017/0446* (2013.01); *A61B 2017/0462* (2013.01)

(56) References Cited

U.S. PATENT DOCUMENTS

| | | | | |
|---|---|---|---|---|
| 2011/0112576 A1* | 5/2011 | Nguyen | ............ | A61B 17/0401 606/232 |
| 2013/0103054 A1* | 4/2013 | Housman | .......... | A61B 17/0401 606/139 |

OTHER PUBLICATIONS

European Examination Application No. 14713671.7-1122 dated May 21, 2019.
Japanese Application No. 2018-213652—Notice of Reasons for Rejection dated Sep. 19, 2019.

\* cited by examiner

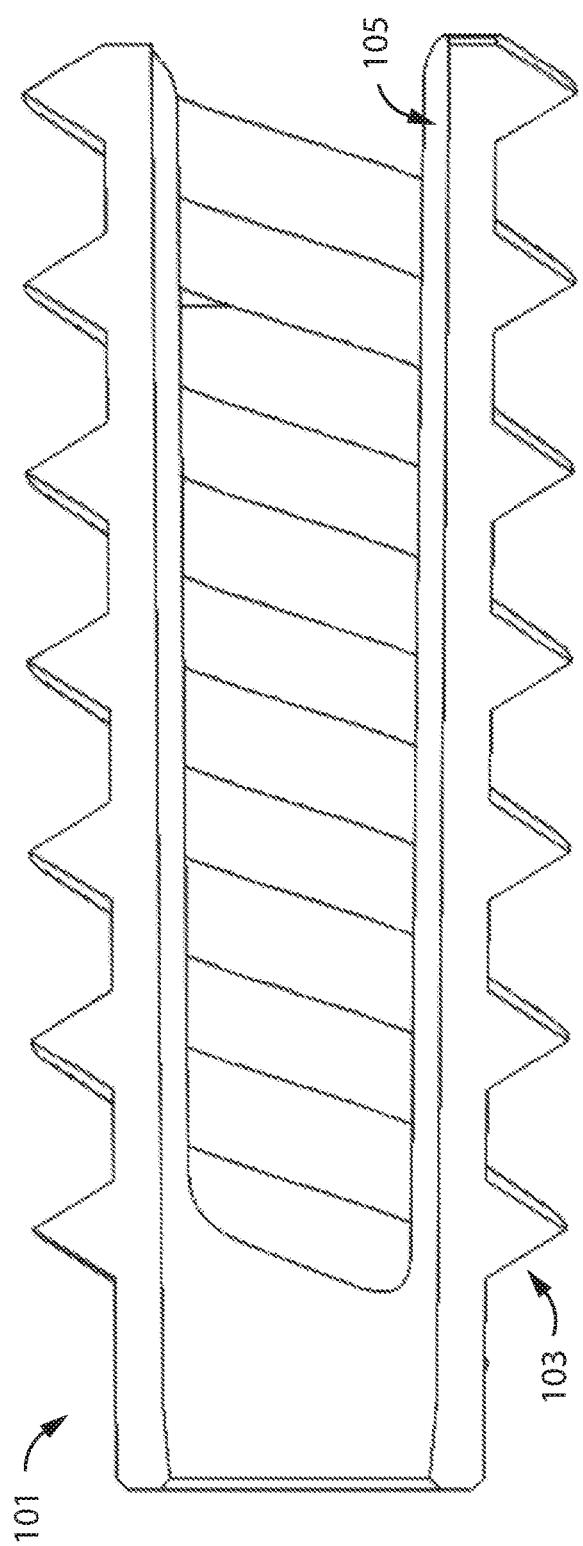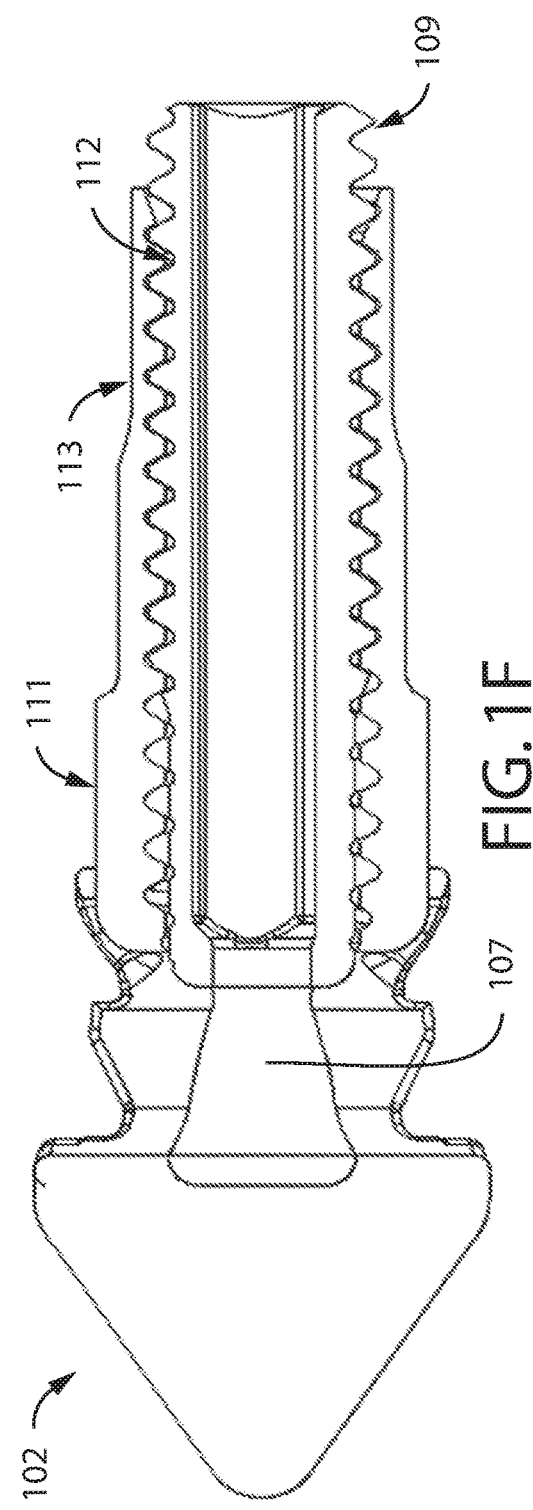
FIG. 1E
FIG. 1F

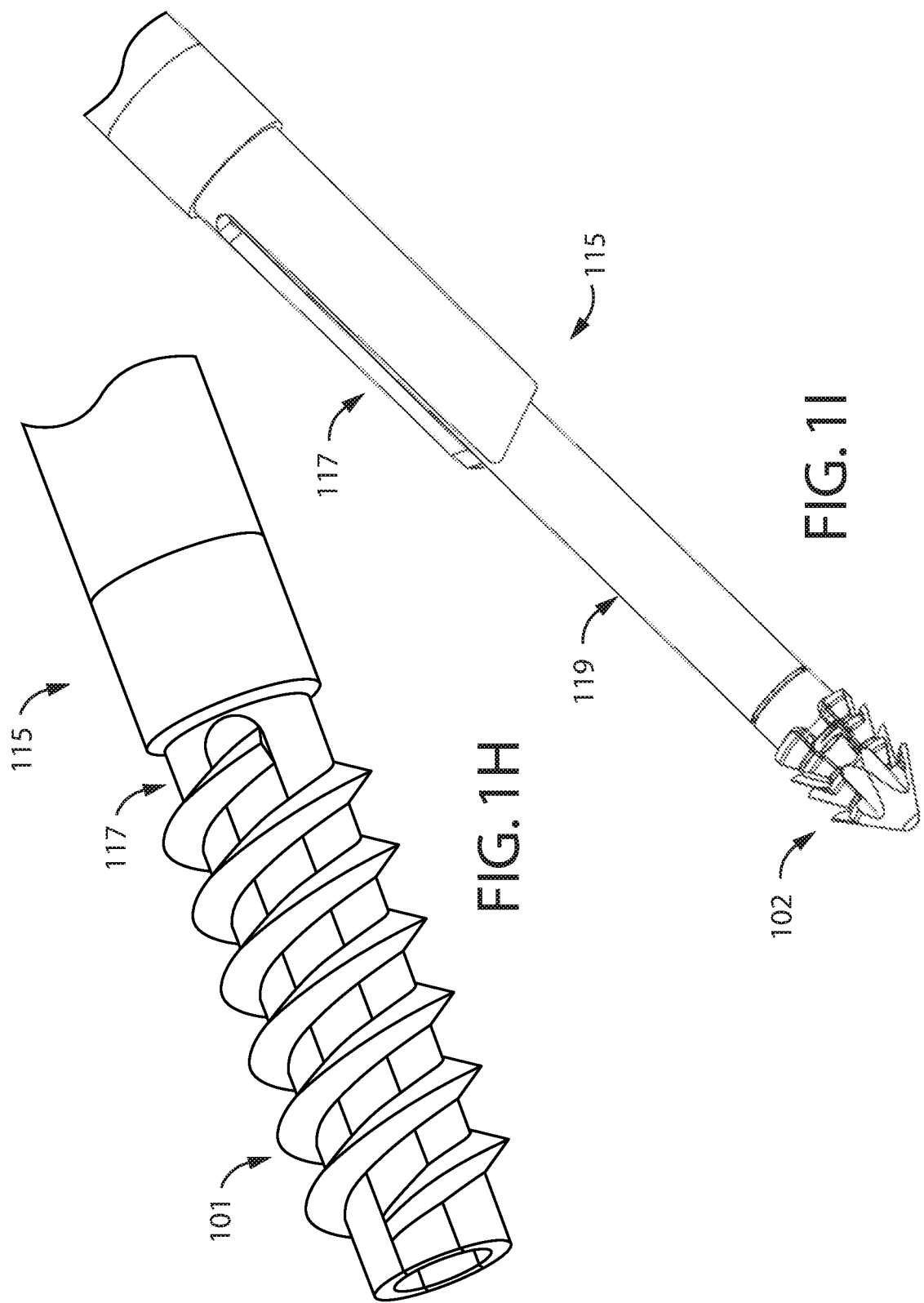

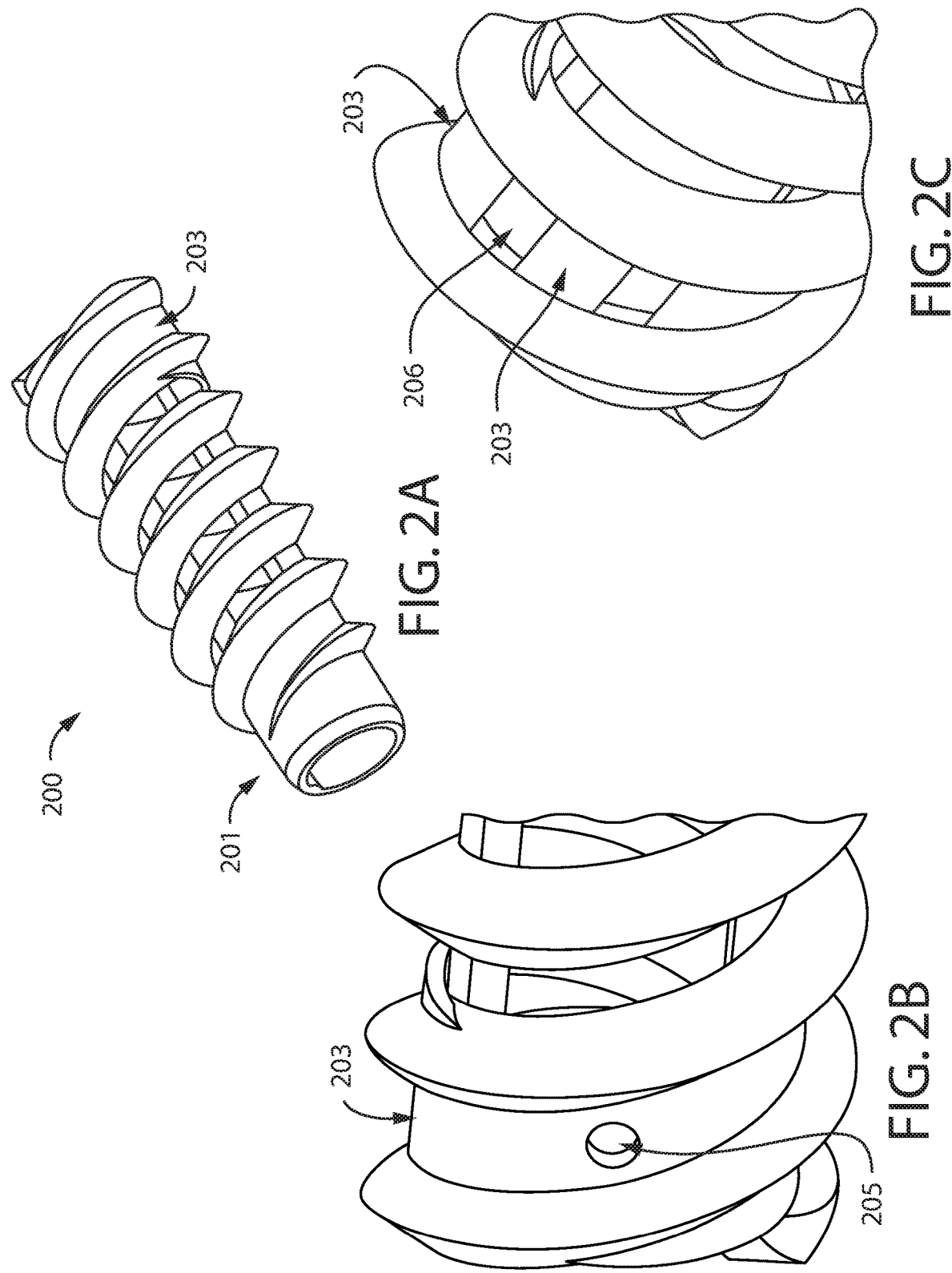

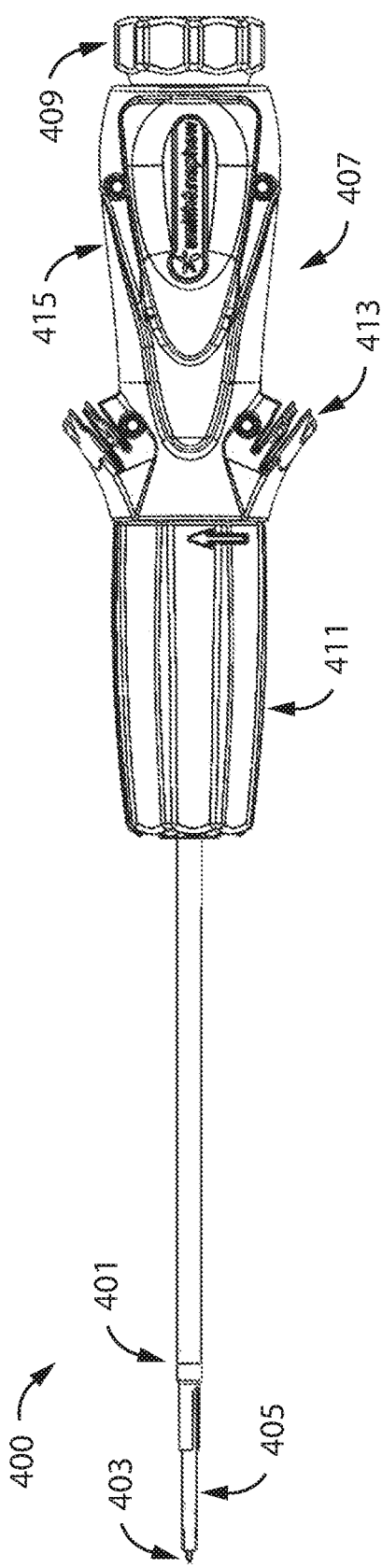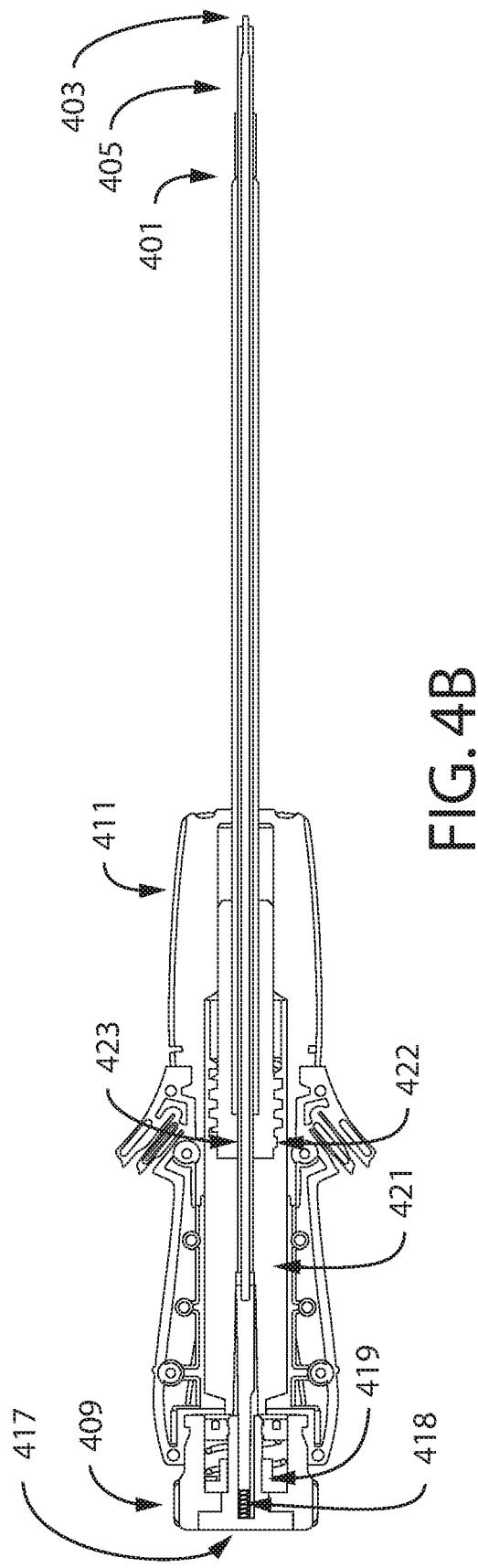
FIG. 4A
FIG. 4B

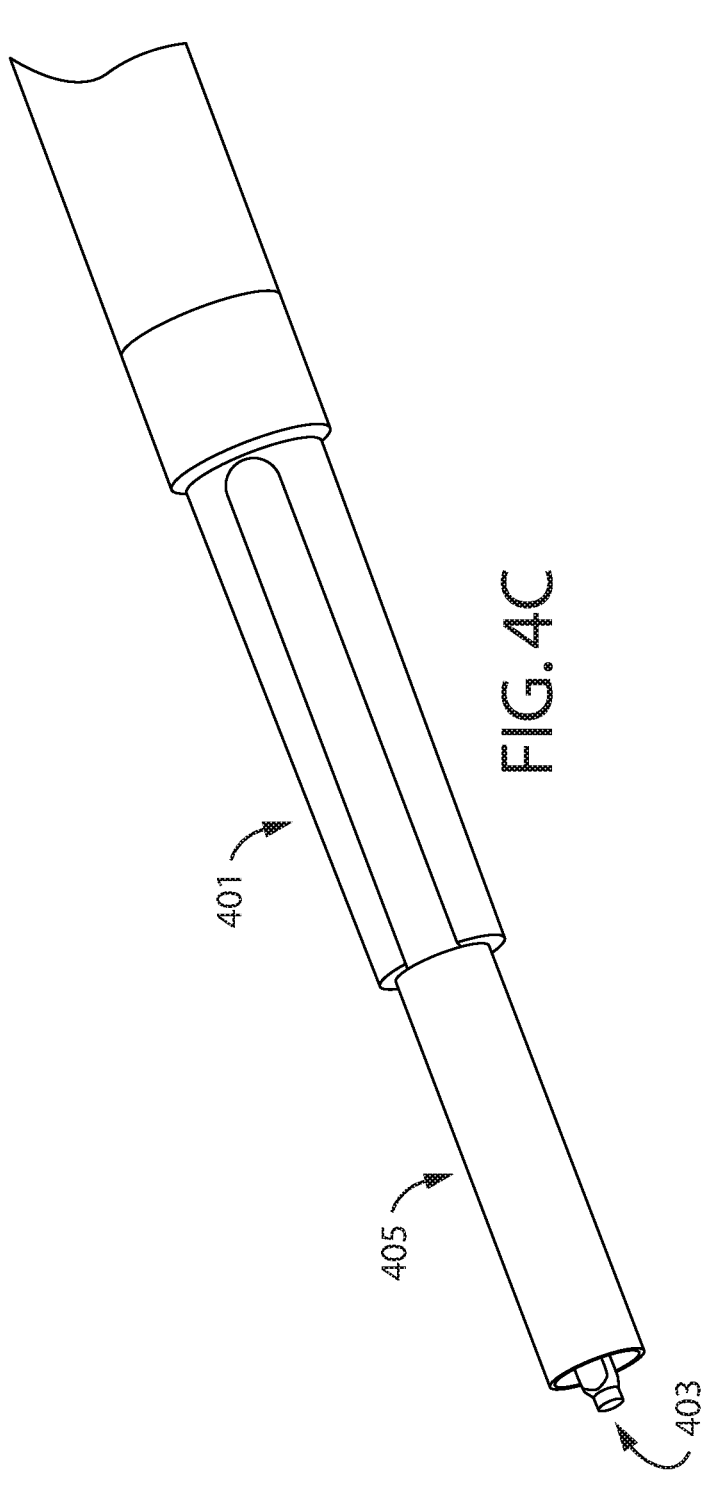
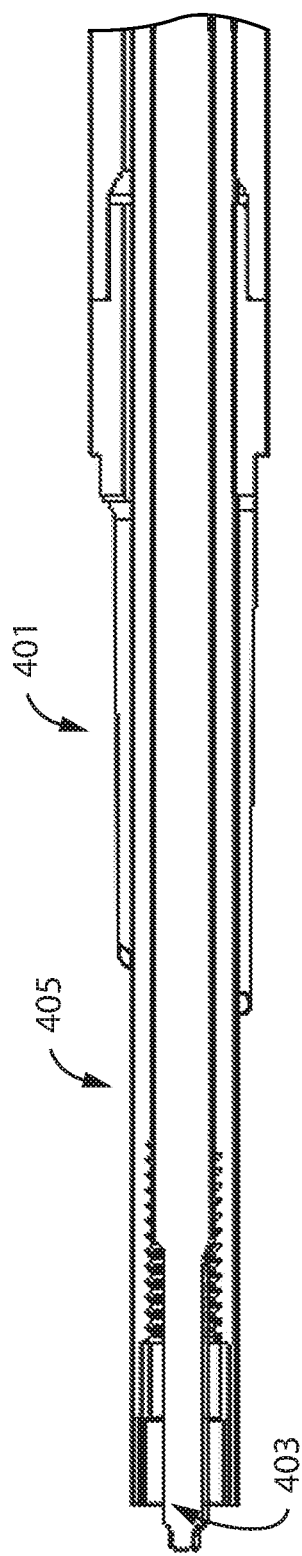
FIG. 4C
FIG. 4D

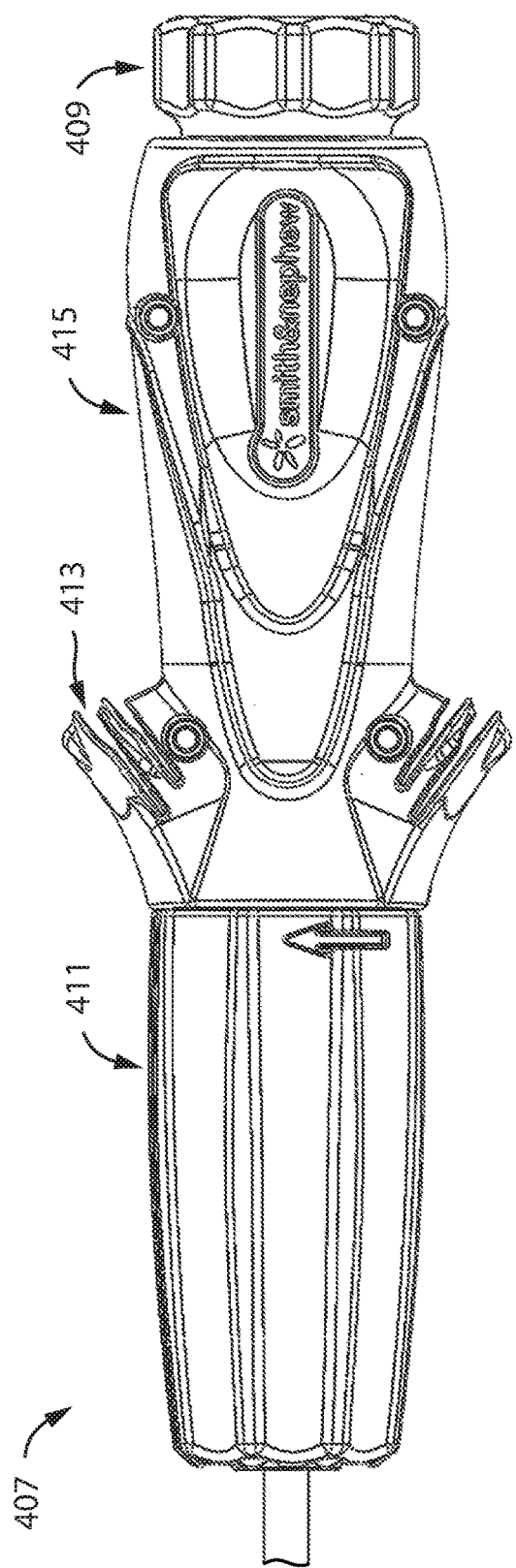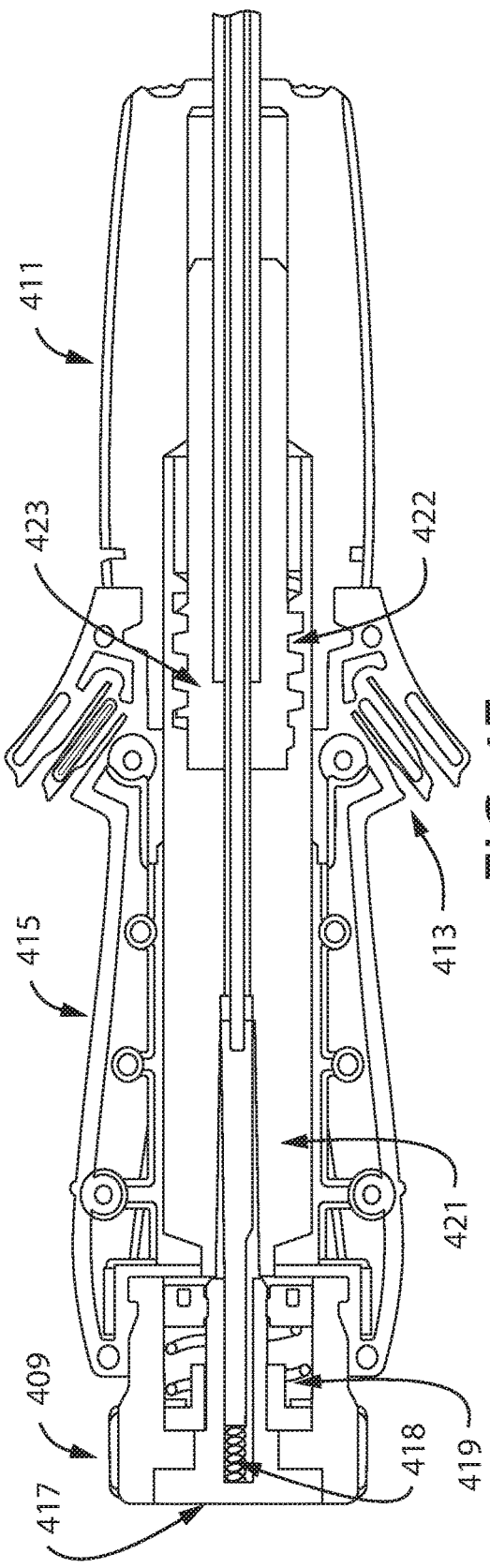

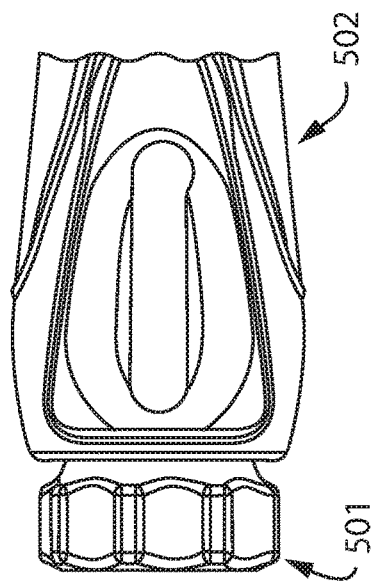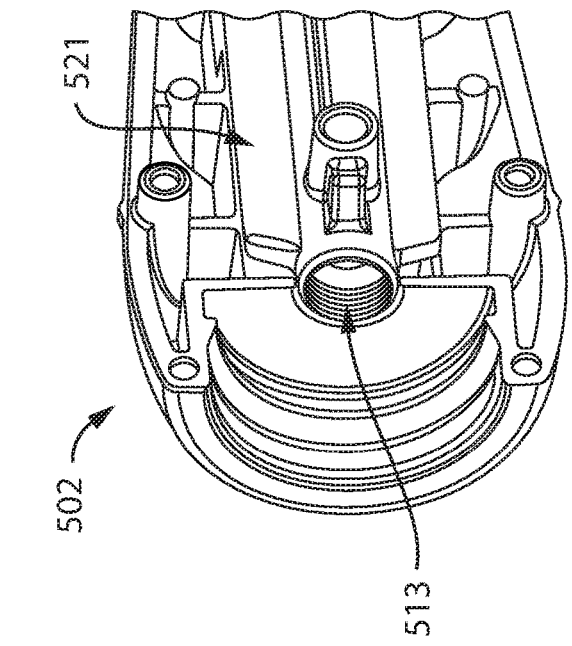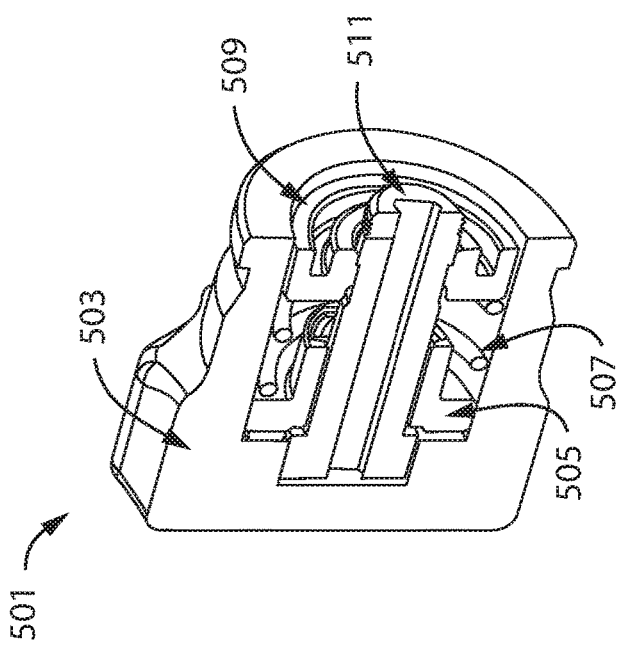

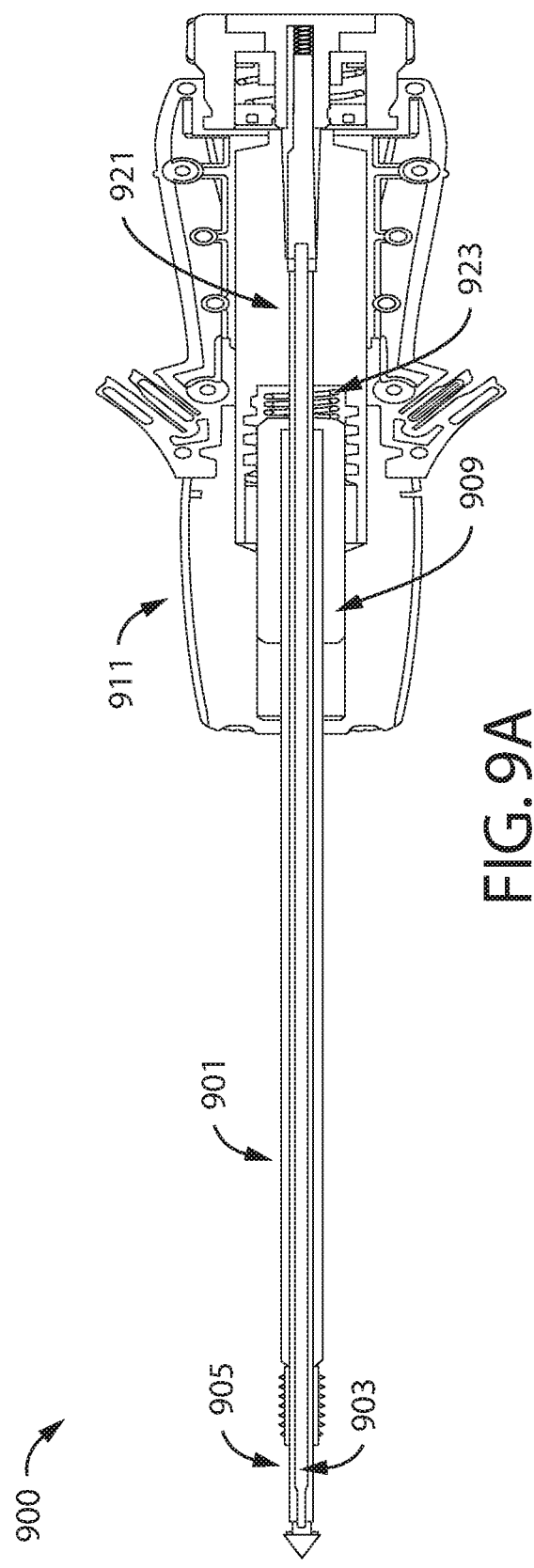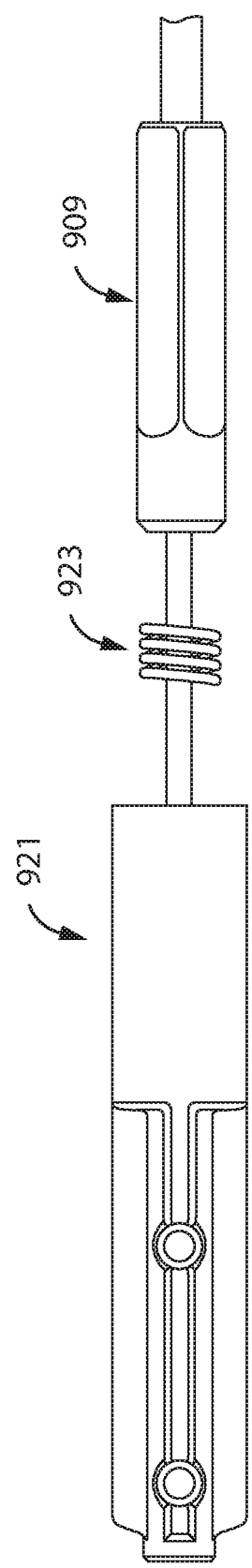
FIG. 9A
FIG. 9B

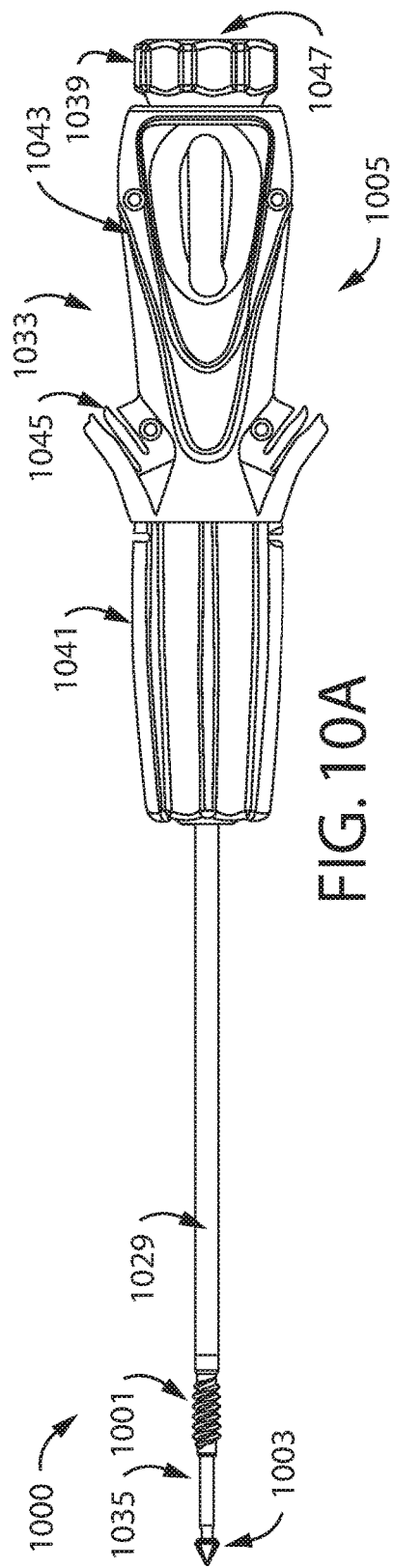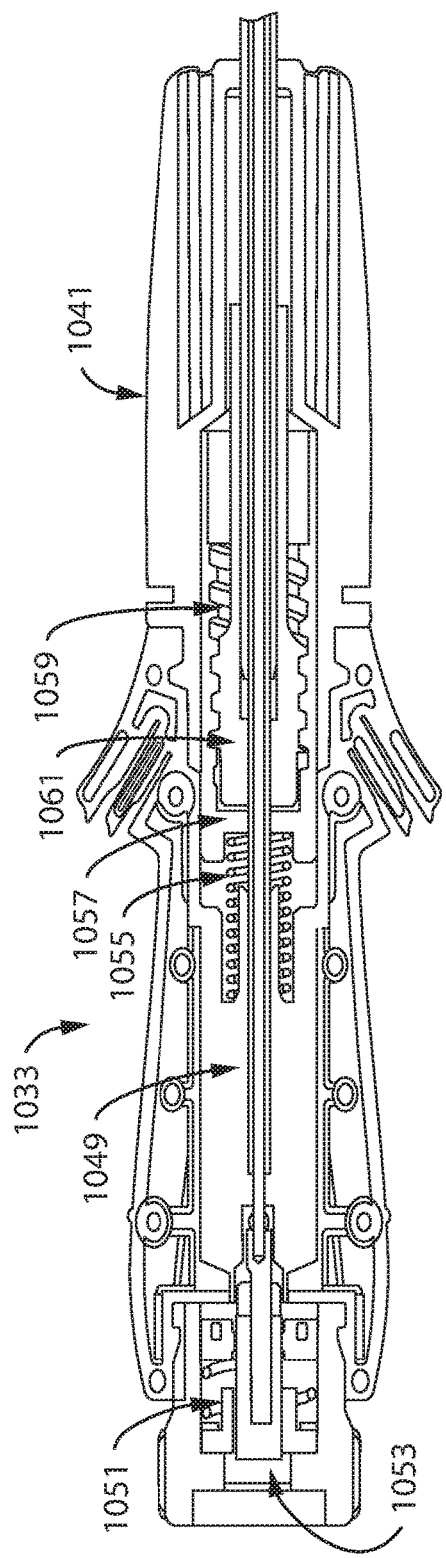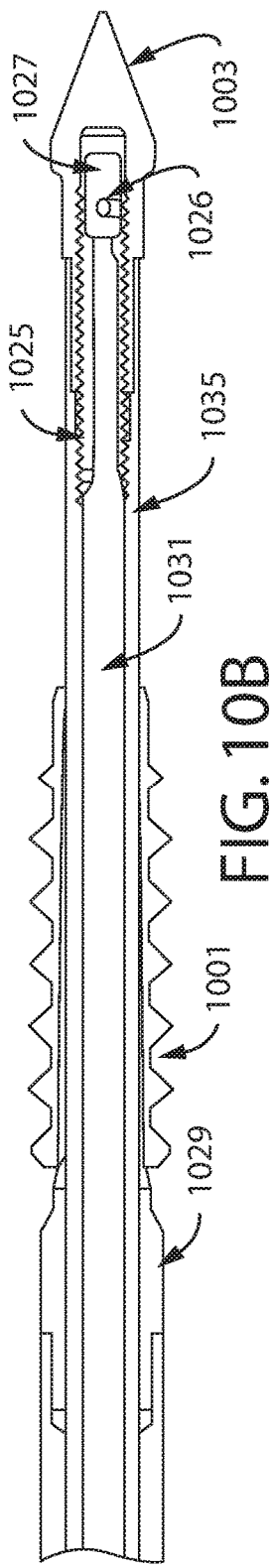
FIG. 10A  FIG. 10B

FENESTRATED LOCKING SUTURE ANCHOR ASSEMBLY

CROSS-REFERENCE TO RELATED APPLICATIONS

This application is a continuation of co-pending U.S. patent application Ser. No. 15/346,980, filed Nov. 9, 2016, entitled FENESTRATED LOCKING SUTURE ANCHOR ASSEMBLY, which in turn is a divisional of U.S. patent application Ser. No. 13/838,729, filed Mar. 15, 2013, now U.S. Pat. No. 9,526,488, the entire contents of which are incorporated herein by reference for all purposes.

FIELD OF THE TECHNOLOGY

The described technology relates generally to tissue repair, and more specifically, to an anchor for securing tissue to bone.

BACKGROUND

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact.

SUMMARY

A procedure, and components for use in such procedure, that securely attaches tissue to bone using a plurality of attachment points over a large area of contact is needed. Such procedure must be able to be done in a quick and efficient manner with a minimum of recovery time for the patient.

In one aspect, the present disclosure relates to an anchor for securing tissue to bone. The anchor includes a sleeve. The sleeve includes at least one open helical coil having a proximal end and a distal end, wherein the at least one open helical coil defines an internal volume communicating with a region exterior to the at least one open helical coil through a spacing between turns of the at least one open helical coil. The sleeve also includes at least one rib disposed within the internal volume, connected to at least two turns of the at least one open helical coil, wherein the at least one rib is engageable with a grooved shaft of an anchor driver. The anchor also includes a tip structure engageable with the sleeve. The tip structure includes a body defining an internal cavity. The body includes a distal region defining an aperture sized to accept a suture, wherein the aperture is connected to the longitudinal internal cavity. The body also includes a proximal region sized to engage the distal end of the sleeve. The tip structure also includes a suture capture member positioned within the internal cavity and advanceable distally through the internal cavity into the aperture to capture the suture in a locked position.

Any of the aspects and/or embodiments described herein can include one or more of the following embodiments. In some embodiments, the at least one open helical coil is a dual lead helical coil. In some embodiments, the anchor includes one or more structural supports disposed between and connected to at least a two distalmost turns of the at least one open helical coil. In some embodiments, the anchor includes one or more structural supports disposed between and connected to at least a two proximalmost turns of the at least one open helical coil. In some embodiments, the anchor includes at least one hole defined by one of the one or more structural supports. In some embodiments, the spacing includes a plurality of spacing sections, wherein each of the plurality of spacing sections is defined between two turns of the at least one open helical coil, each of the plurality of spacing sections having one structural support disposed therein and extending over a portion thereof, the one structural support being connected to two turns of the at least one open helical coil.

In one aspect, the present disclosure relates to an anchor driver for inserting the anchor into the bone. The anchor driver includes a grooved outer shaft engageable with a sleeve. The anchor driver also includes an inner shaft engageable with a suture capture member of a tip structure. The anchor driver also includes a handle assembly. The handle assembly includes a suture capture advancement member operatively coupled to the inner shaft, wherein the suture capture advancement member advances the suture capture member into a distal, suture-locked position. The handle assembly also includes a sleeve advancement member operatively coupled to the grooved outer shaft, wherein the sleeve advancement member advances the sleeve into engagement with the tip structure.

Any of the aspects and/or embodiments described herein can include one or more of the following embodiments. In some embodiments, the anchor driver includes an intermediate shaft positioned between the grooved outer shaft and the inner shaft, the intermediate shaft being releasably attachable to the tip structure. In some embodiments, the anchor driver includes a visual marker disposed on at least one of the intermediate shaft or the inner shaft. In some embodiments, the handle assembly further comprises a pounding surface for pounding the distal region of the body of the tip structure into a bone.

In some embodiments, the handle assembly includes an axially yielding interface configured to allow a relative motion between the grooved outer shaft and the inner shaft along a longitudinal axis of the anchor driver. In some embodiments, the relative motion between the grooved outer shaft and the inner shaft is a response to a threshold force exerted along the longitudinal axis of the anchor driver. In some embodiments, the axially yielding interface includes at least one of a spring, an elastic member, a ratcheting mechanism, or a hydraulic piston.

In some embodiments, the suture capture advancement member includes a torque limiter for limiting a maximum torque applicable to the inner shaft. In some embodiments, the suture capture advancement member includes a threaded depth stop for limiting a maximum travel of the inner shaft. In some embodiments, the suture capture advancement member includes a torque limiter for limiting a maximum torque applied to the inner shaft and a threaded depth stop for limiting a maximum travel of the inner shaft.

In one aspect, the present disclosure relates to a system for tissue repair. The system for tissue repair includes an anchor for securing tissue to bone. The anchor includes a sleeve. The sleeve includes at least one open helical coil having a proximal end and a distal end, wherein the at least one open helical coil defines an internal volume communicating with a region exterior to the at least one open helical coil through a spacing between turns of the at least one open helical coil. The sleeve also includes at least one rib disposed within the internal volume, connected to at least two turns of the at least one open helical coil, wherein the at least one rib is engageable with a grooved shaft of an anchor driver. The system for tissue repair also includes a tip structure engageable with the sleeve. The tip structure includes a body defining an internal cavity. The body includes a distal region defining an aperture sized to accept a suture, wherein the aperture is connected to the longitudinal internal cavity. The body also includes a proximal region sized to engage the distal end of the sleeve. The tip structure also includes a suture capture member positioned within the internal cavity and advanceable distally through the internal cavity into the aperture to capture the suture in a locked position.

The system for tissue repair also includes an anchor driver for inserting the anchor into the bone. The anchor driver includes a grooved outer shaft engageable with the at least one rib of the sleeve. The anchor driver also includes an inner shaft engageable with the suture capture member of the tip structure. The anchor driver also includes a handle assembly. The handle assembly includes a suture capture advancement member operatively coupled to the inner shaft, wherein the suture capture advancement member advances the suture capture member into a distal, suture-locked position. The handle assembly also includes a sleeve advancement member operatively coupled to the grooved outer shaft wherein the sleeve advancement member advances the sleeve into engagement with the tip structure.

Any of the aspects and/or embodiments described herein can include one or more of the following embodiments. In some embodiments, a distal end of the sleeve, the sleeve being substantially engaged with the grooved outer shaft but not engaged with the tip structure, and a surface of a bone into which the tip structure has been driven by the anchor driver define an axial clearance along a longitudinal axis of the anchor driver.

In one aspect, the present disclosure relates to a method of tissue repair. The method includes providing an anchor system for securing tissue to bone. The anchor system includes a sleeve. The sleeve includes at least one open helical coil having a proximal end and a distal end wherein the at least one open helical coil defines an internal volume communicating with a region exterior to the at least one open helical coil through a spacing between turns of the at least one open helical coil. The sleeve also includes at least one rib disposed within the internal volume, connected to at least two turns of the at least one open helical coil, wherein the at least one rib is engageable with a grooved outer shaft of an anchor driver. The anchor system also includes a tip structure engageable with the sleeve. The tip structure includes a body defining an internal cavity. The body includes a distal region defining an aperture sized to accept a suture, wherein the aperture is connected to the internal cavity. The body also includes a proximal region sized to engage the distal end of the sleeve. The tip structure also includes a suture capture member positioned within the internal cavity and advanceable distally through the internal cavity into the aperture to capture the suture in a locked position. The method also includes driving the tip structure into a bone using the anchor driver. The method also includes advancing, using the anchor driver, the suture capture member into a distal, suture-locked position to capture the suture in a locked position. The method also includes advancing the sleeve into the bone and into engagement with the tip structure using the anchor driver.

Any of the aspects and/or embodiments described herein can include one or more of the following embodiments. In some embodiments, the method includes retracting, using the anchor driver, the suture capture member into a proximal, suture-unlocked position to release the suture into a freely slidable state. In some embodiments, the method includes engaging the at least one rib of the sleeve with the grooved outer shaft of the anchor driver. In some embodiments, the method includes engaging the suture capture member of the tip structure with an inner shaft of the anchor driver. In some embodiments, the method includes releasably attaching the tip structure to an intermediate shaft of the anchor driver positioned between the grooved shaft and the inner shaft. In some embodiments, the method includes exerting a threshold force along a longitudinal axis of the anchor driver, causing a retraction of the grooved shaft of the anchor driver. In some embodiments, advancing the sleeve includes axially sliding the sleeve along a longitudinal axis of the anchor driver.

In some embodiments, the anchor driver includes a housing defining a threaded internal cavity coupled with the grooved outer shaft for providing a threaded travel of the sleeve relative to the inner shaft, wherein advancing the sleeve is achieved by rotating the housing. In some embodiments, driving the tip structure results in an axial clearance defined along the longitudinal axis of the anchor driver between a surface of the bone and a distal end of the sleeve, the sleeve being substantially engaged with the grooved outer shaft. In some embodiments, the threaded travel of the sleeve is equal to or greater than the axial clearance. In some embodiments, the housing is slidable relative to the inner shaft along the longitudinal axis of the anchor driver for providing a slidable travel of the sleeve. In some embodiments, the slidable travel of the sleeve is equal to or greater than the axial clearance. In some embodiments, a combined travel of the sleeve, comprising the slidable travel of the sleeve added to the threaded travel of the sleeve, is equal to or greater than the axial clearance. In some embodiments, at least one of the sleeve, the housing, or the grooved outer shaft further comprises one or more locking mechanisms for preventing a longitudinal sliding motion of the housing.

The procedure, and components for use in such procedure, for attaching tissue to bone (hereinafter "technology") can provide one or more of the following advantages. One advantage of the technology is that patient recovery time is advantageously minimized because the open helical coil structure and/or fenestrations of various anchor components promotes bony ingrowth, thereby accelerating bone recovery. Another advantage of the technology is that the anchor driver provides for rapid, efficient, knotless insertion of the anchor into bone. The technology advantageously provides sufficient structural support, impact avoidance mechanisms, and/or impact absorption mechanisms to prevent breakage of anchor and/or anchor driver components.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The foregoing and other objects, features, and advantages will be apparent from the following more particular description of the embodiments as illustrated in the accompanying drawings in which like reference characters refer to the same parts throughout the different views. The drawings are not necessarily to scale, emphasis instead being placed upon illustrating the principles, characteristics, and features of the embodiments. In the drawings:

FIGS. 1A-1I are isometric and cross-sectional views illustrating components of an anchor assembly in accordance with various embodiments.

FIGS. 2A-2C are isometric views illustrating proximal and distal structural supports in accordance with various embodiments.

FIGS. 4A-4F are isometric and cross-sectional views illustrating components of an anchor driver in accordance with various embodiments.

FIGS. 5A-5C are isometric and cross-sectional views illustrating components of a torque and/or travel limiter in accordance with various embodiments.

FIGS. 9A-9D are isometric and cross-sectional views illustrating an axially compliant anchor driver in accordance with various embodiments.

FIGS. 10A-10D are isometric and cross-sectional views illustrating a system for tissue repair in accordance with various embodiments.

DETAILED DESCRIPTION

Figure 1A:
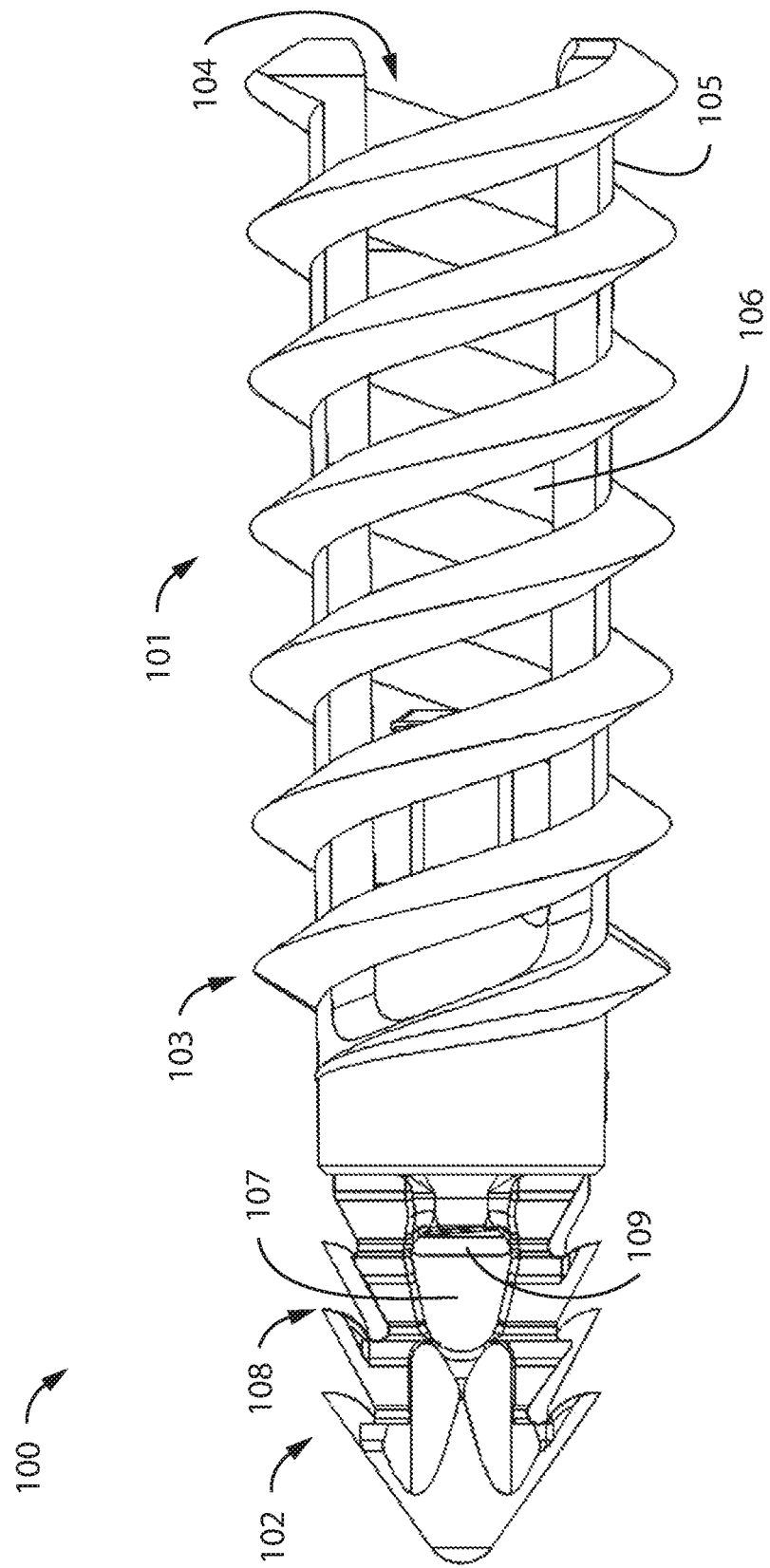
Figure 1B:
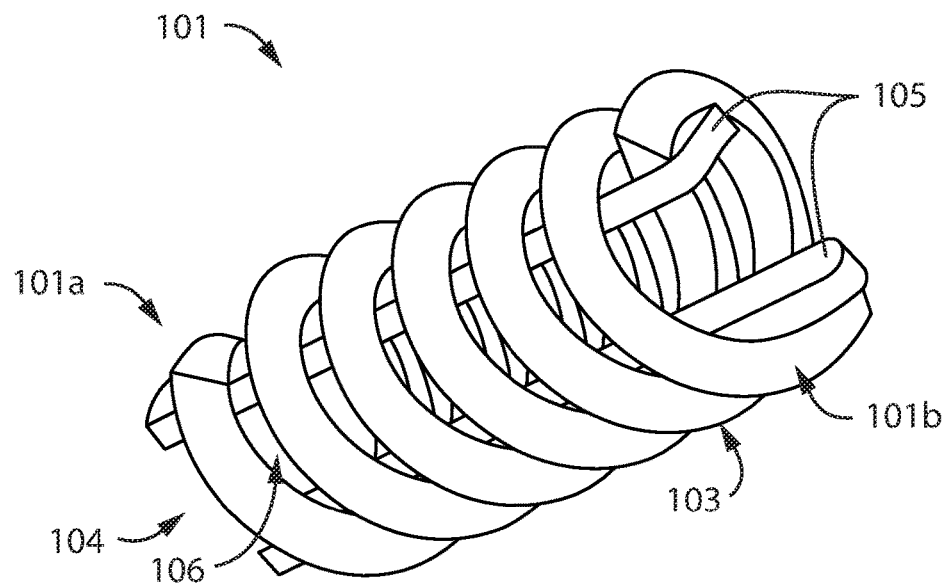

The following description of the preferred embodiment(s) is merely exemplary in nature and is in no way intended to limit the disclosure, its application, or uses.

FIGS. 1A-1I show isometric and cross-sectional views of components of an anchor assembly 100 for securing a tissue to bone in accordance with various embodiments. The anchor assembly 100 includes a sleeve 101 and a tip structure 102. In some embodiments, the tip structure 102 is pounded into the bone to insert a suture into the bone and the sleeve 101 is screwed or otherwise advanced into the bone over the tip structure 102 to securely lock the tip structure into the bone. The sleeve 101 includes at least one open helical coil 103 having a plurality of open spacing sections 106 between turns of the open helical coil 103 for allowing bony ingrowth from the bone into an internal volume 104 defined within the open helical coil 103 and also includes at least one rib 105 (two as shown) connected to at least two turns of the open helical coil 103.

The tip structure 102 includes a body 110 having a distal portion 110a and a proximal portion 110b, an internal cavity 112 defined within the body 110, a suture capture member 109 advanceable through the internal cavity 112 to lock one or more sutures in an aperture (eyelet) 107. The aperture 107, in accordance with various embodiments, is defined within the body 110 for receiving and retaining one or more sutures. The distal portion 110a can, in various embodiments, terminate in a pointed and/or barbed tip for breaking through bone during insertion. The distal portion 110a can also be rounded or flat-ended for various embodiments where, for example pre-drilling of the bone obviates the need for a distal, terminal point.

Figure 1C:
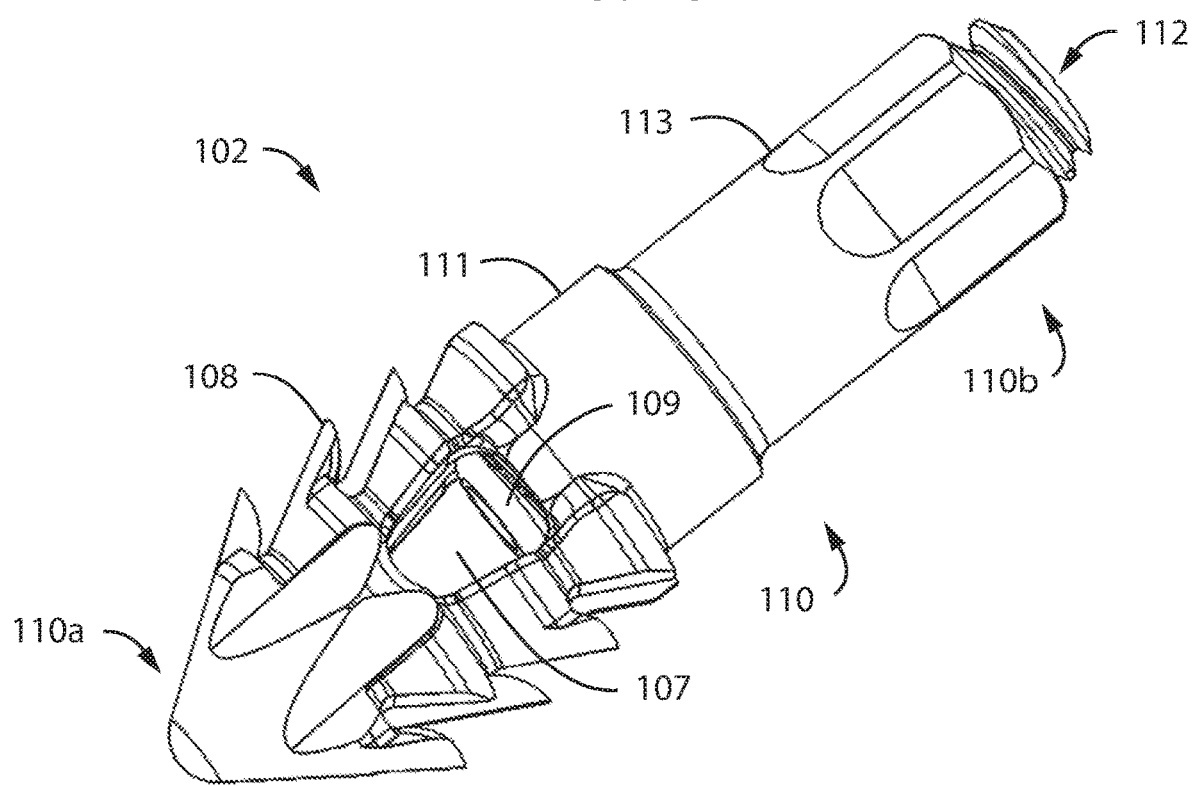
Figure 1D:
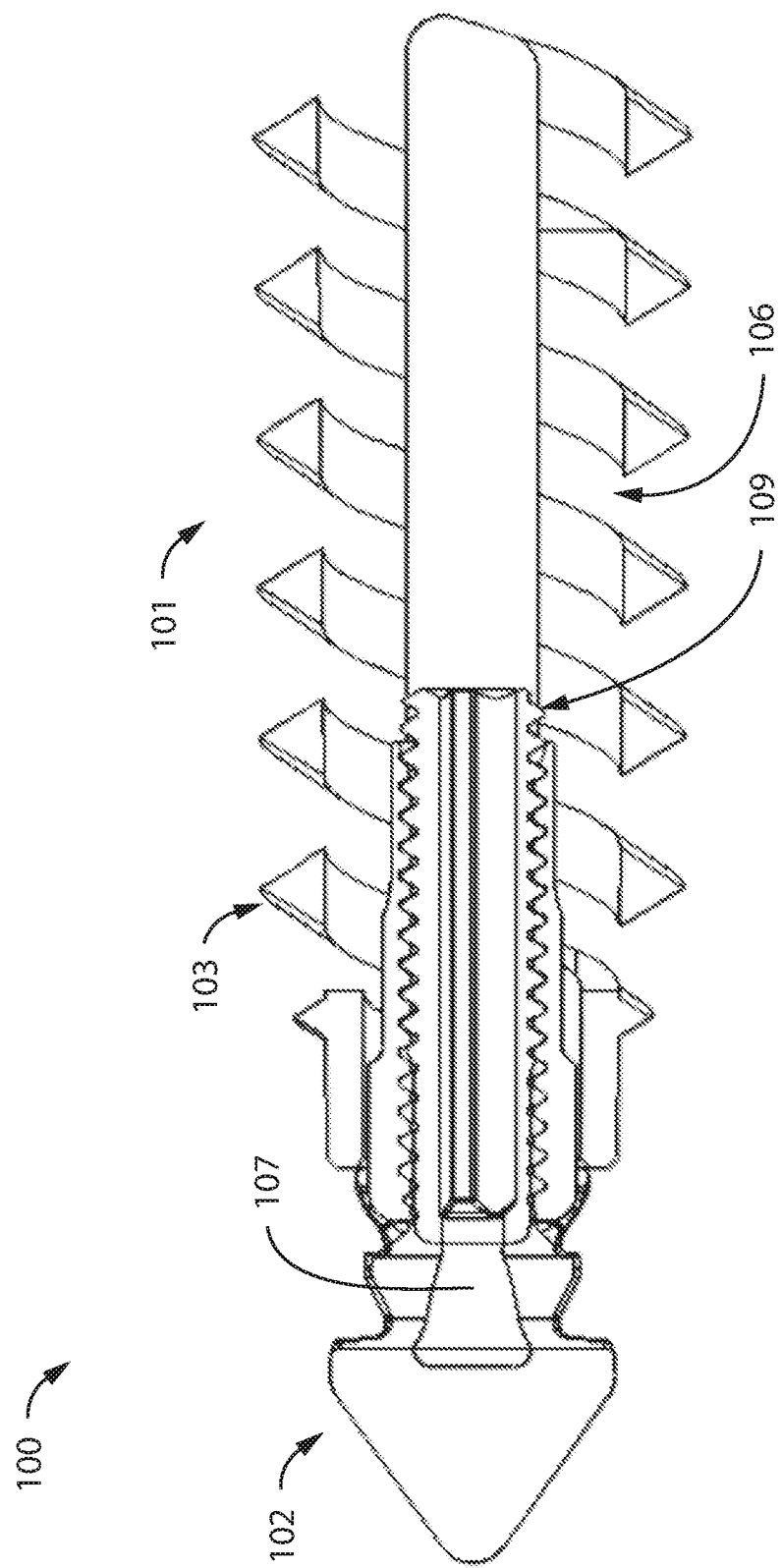
Figure 1G:
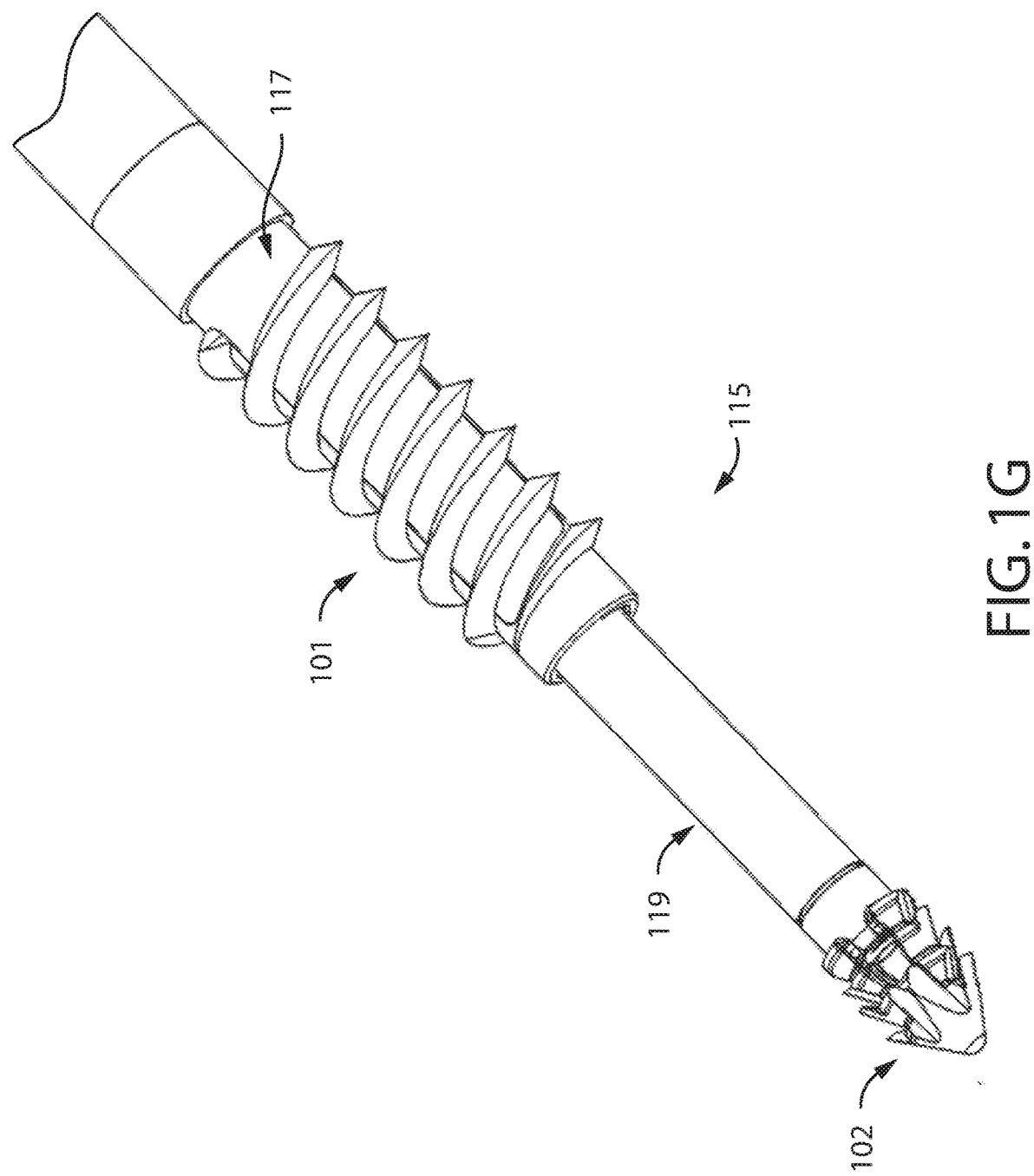

As shown in FIGS. 1G-1I, the anchor assembly 100 can be installed, for example, into a bone (not shown) using an anchor driver 115. Anchor drivers 115 in accordance with various embodiments can include a grooved outer shaft 117 insertable into the internal volume 104 of the sleeve 101 and engageable with the ribs 105. Anchor drivers 115 used to install the anchor assembly 100 can be but are not limited to, any of the anchor drivers described below with reference to FIGS. 4-9.

The sleeve 101 can be constructed from, for example but not limited to, polymers (e.g., PEEK), bioabsorbable materials, metals (e.g., surgical steel, titanium), or any other suitable material. For weaker, more brittle materials such as for example, bioabsorbable materials, a purely open helical coil design (e.g., 103 can be insufficient to support the various forces and stresses endured by an anchor, requiring structural supports to be added. As shown in FIG. 2A, a sleeve 200 can, in various embodiments, include one or more distal structural supports 201 connected to at least the two distalmost turns of the open helical coil (e.g., 103). As shown in FIGS. 2A-2C, various embodiments can include one or more proximal structural supports 203 connected to the at least the two proximalmost turns of the open helical coil. In some embodiments, one or more fenestrations 205 can be defined by the proximal structural support(s) 203 to support at least some bony ingrowth properties in the areas of the proximal structural supports 203 and/or distal structural supports 201.

Figure 3:
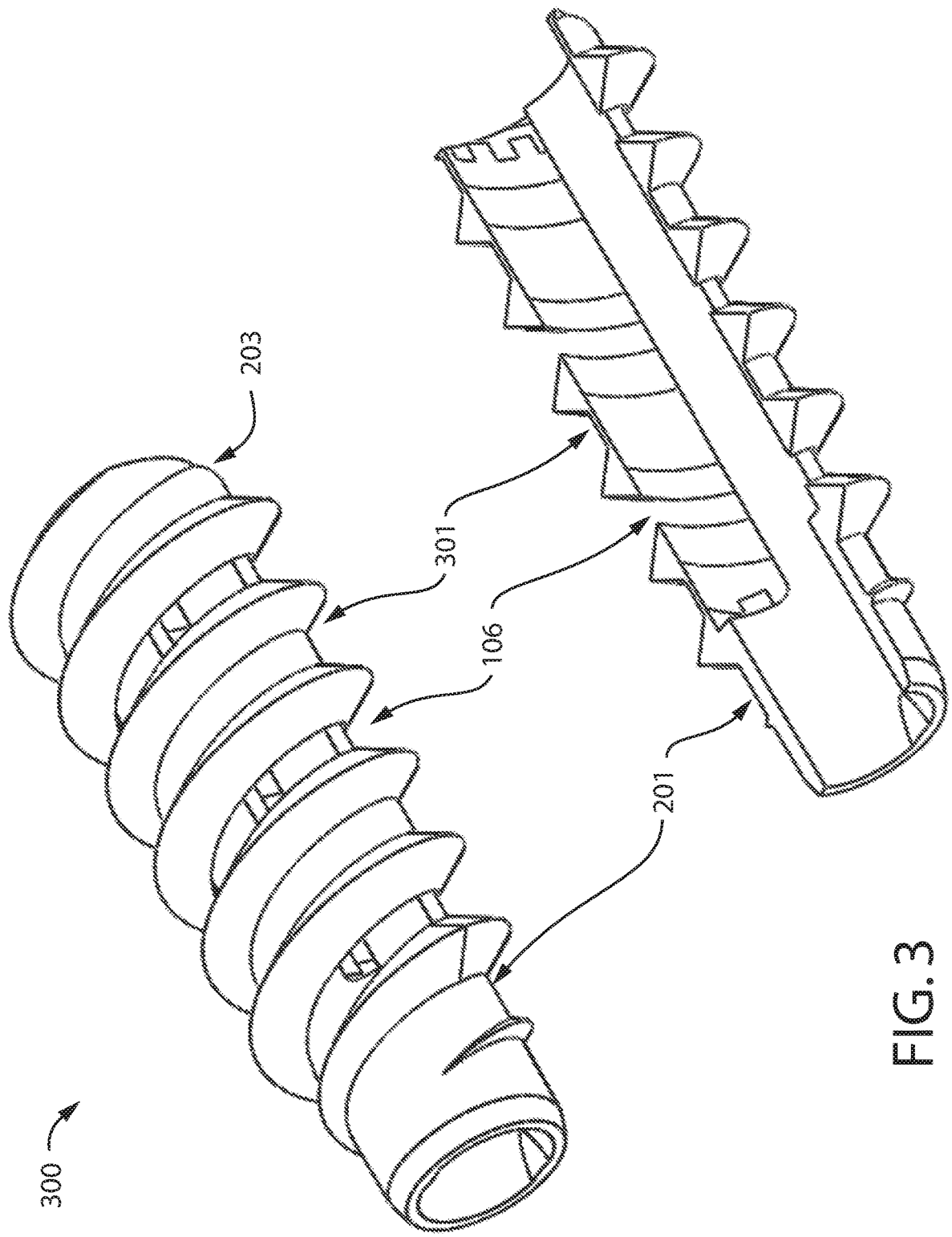
FIG. 3 provides isometric and cross-sectional views illustrating circumferential structural supports in accordance with various embodiments.

Similarly, in some embodiments, bony ingrowth can be supported by distributing multiple proximal structural supports 203 about the circumference of the two proximalmost turns of the open helical coil in order to define open segments 206 between each proximal structural support 203. Alternatively, as shown in FIG. 3, sleeves in accordance with various embodiments can include one or more circumferential structural supports 301, each connected to two turns of the open helical coil, within each of the plurality of open spacing sections 106 for providing added structural integrity while still promoting bony ingrowth.

The tip structure 101 can be constructed from, for example but not limited to, polymers (e.g., PEEK), bioabsorbable materials, metals (e.g., surgical steel, titanium), or any other suitable material. As shown in FIGS. 1C and 1F, the distal region 110a of the body 110 of the tip structure 102 can be substantially conically shaped for better penetration of the bone and can, in various embodiments, include barbs 108 protruding therefrom to improve pullout strength. In some embodiments, the proximal region 110b of the body 110 includes a sleeve engagement surface 111 for engaging with the distal end 101a of the sleeve 101, 200, 300 after the sleeve 101, 200, 300 has been screwed down over the tip structure 102. In various embodiments, the proximal region 110b includes an intermediate shaft engagement surface 113 for engaging with an intermediate (middle) shaft 119 of the anchor driver 115.

FIGS. 4A-4F illustrate an anchor driver 400 in accordance with various embodiments. The anchor driver 400 includes an outer shaft 401 for engaging with a sleeve (e.g., 101) or other outer structure, an inner shaft 403 for engaging with a tip structure (e.g., 102), and a handle assembly 407 for holding and operating the anchor driver 400. In various embodiments, the anchor driver 400 can also include one or more intermediate shafts 405 to, for example, provide additional stiffness when pounding in a tip structure.

The outer shaft 401 can, for example, be grooved and can be configured to engage one or more components of an anchor assembly (e.g., the internal volume 104 and ribs 105 of the sleeve 101 of anchor assembly 100 as described above with reference to FIGS. 1-3). The inner shaft 403 can be, in some embodiments, configured to engage one or more components of an anchor assembly (e.g., the suture capture member 109 of the anchor assembly 100 described above with reference to FIGS. 1-3). The intermediate shaft 405 can be, in some embodiments, configured to engage a component of an anchor assembly 100 (e.g., the intermediate shaft engagement surface 113 of the tip structure of the anchor assembly 100 described above with reference to FIGS. 1-3).

As shown in FIGS. 4E and 4F, the handle assembly 407 includes a suture capture advancement member 409 (e.g., a knob as shown) for advancing a suture capture member to capture a suture, a sleeve advancement member 411 (e.g., a collar as shown) for screwing in a sleeve (e.g., 101), a handle grip 415 for holding and/or maneuvering the anchor driver during insertion of the anchor (e.g., 100) into bone, one or more suture slots 413 protruding from the handle grip 415 for placing and/or maintaining tension on a suture during installation of the anchor into bone. The handle assembly 407 also includes, a pounding surface 417 for pounding a tip structure (e.g., 102) into bone, and a center housing 421.

In various embodiments, the suture capture advancement member 409 can include a torque and/or travel limiter 419, which can be but is not limited to, a torque and/or travel limiter 501 as described below with reference to FIGS. 5A-5C. In some embodiments, the suture capture advancement member 409 defines a threaded inner shaft receiving cavity 418, which is counter-threaded with a proximal section of the inner shaft 403. In such embodiments, rotating or twisting the suture capture advancement member 409 rotates the proximal section of the inner shaft 403, thereby causing the inner shaft 403 to advance distally through the threaded inner shaft receiving cavity 418 and, consequently, advancing the suture capture member (e.g., 109) to lock one or more sutures in place.

In some embodiments, the center housing 421 defines a threaded drive hub receiving cavity 422, which is counter-threaded with an outer drive hub 423. The outer drive hub 423 can be affixed to a proximal end of the outer shaft 401 and be engaged with the sleeve advancement member 411. In such embodiments, twisting or rotating the sleeve advancement member 411 rotates the outer drive hub 423, thereby causing the outer drive hub 423 to advance distally through the threaded drive hub receiving cavity 422, and, consequently, advancing the outer shaft 401 relative to the inner shaft 403, thereby advancing the sleeve (e.g., 101, 200, 300) into engagement with the tip structure (e.g., 102).

In various embodiments, the handle grip 415, suture capture advancement member 409, sleeve advancement member 411, center housing 421, and/or outer drive hub 423 can each be manufactured from a polymer material and via an injection molding process. However, any other suitable material (e.g., metals, composites, wood) and/or process (e.g., extrusion, machining, electro-chemical machining) can be used. The handle grip 415, suture capture advancement member 409, and/or sleeve advancement member 411 can be coupled via an interference fit. However, any other suitable method of coupling (e.g., screws, adhesives, rivets) can be used.

The components of outer shaft 401, inner shaft 403, and/or intermediate shaft(s) 405 can be made from a metal material via an extrusion or drawing process. However, any other suitable material (e.g., plastics, composites) and/or process (e.g., injection molding, casting, machining, electro-chemical machining) can be used. The components of outer shaft 401, inner shaft 403, and/or intermediate shaft(s) 405 can be coupled to the handle grip 415, suture capture advancement member 409, and/or sleeve advancement member 411 via an interference fit. However, any other suitable method of coupling (e.g., screws, adhesives, rivets) can be used.

In various embodiments, turning the suture capture advancement member 409 advances the inner shaft 403, which is engaged with a suture capture member (e.g., 109 as shown in FIG. 1). Consequently, turning the suture capture advancement member 409 also advances the suture capture member. As advancement continues, one or more sutures in an aperture (e.g., 107 as shown in FIG. 1) can be compressed by the suture capture member, increasing the torque required to turn the suture capture advancement member 409 until, ultimately, the suture capture member (e.g., 109) either stops or fails. Applying excessive torque to the suture capture advancement member 409 and, consequently, excessive axial force to the inner shaft 403 and the suture capture member can result in breakage of one or more components of the anchor (e.g., 100) or anchor driver (e.g., 400 as shown in FIG. 4, 600 as shown in FIG. 6, and/or 900 as shown in FIG. 9). Accordingly, as shown in FIGS. 5A-5C, various embodiments can advantageously include a torque and/or travel limiter 501 to stop advancement of the suture capture member upon reaching or exceeding a maximum torque and/or depth threshold. The torque and/or travel limiter 501 can, in various embodiments, be incorporated into a suture capture advancement member 409. In some embodiments, the torque and/or travel limiter 501 includes an outer housing 503, a threaded shaft 511, a pawl 505 and spring 507 torque limiter, and a ring 509 for distributing an axial force applied to the torque and/or travel limiter 501. The outer housing 503 can be, in various embodiments, rotably retained by a handle grip 502 of the anchor driver.

The pawl 505, in various embodiments, can be held by the spring 507 against a notch (not shown) on the circumference of the threaded shaft 511. In such embodiments the spring 507 can be designed such that the holding force of the spring 507 is overcome when a torque equal to or greater than a threshold torque (e.g., 1.2 in-lbf, 3.2 in-lbf, or any other desired threshold torque) is applied to the suture capture advancement member 409. Overcoming the holding force of the spring results in release of the pawl 505 and allows the outer housing 503 to spin freely about the threaded shaft 511. In various embodiments, the movement of the pawl 505 over one or more notches causes an audible clicking sound, alerting a user that the suture capture member has been fully advanced. Although a pawl and spring torque limiter is described herein for illustrative purposes, it will be apparent in view of the present disclosure that any suitable torque limiter can be used (e.g., shear pin, synchronous magnetic, ball detent, friction plate).

The threaded shaft 511, in various embodiments, can be threaded along at least a portion of the length of the shaft 511. The threads of the threaded shaft 511 can, in some embodiments, engage with receiving threads in a housing 521. In such embodiments, the length of the threaded portion of the threaded shaft 511 sets a maximum travel of the suture capture member. Therefore, the threaded shaft 511 provides a positive depth stop to prevent excessive advancement of the suture capture member. Upon reaching the positive depth stop, the torque required to turn the suture capture engagement member 409 rapidly increases. In some embodiments, the additional required torque causes the spring 507 to release the pawl 505, thereby producing an audible clicking sound. It will be apparent in view of the present disclosure that any arrangement of a threaded member and receiving threads can be suitable, including, for example, receiving threads on the handle 502, the threaded member being incorporated into the outer housing 503, and/or any other suitable arrangement.

It will further be apparent in view of the present disclosure that various embodiments cannot include both a torque limiter and a positive depth stop but can instead include only a torque limiter or only a positive depth stop. In various embodiments, other auditory, tactile, or other sensory feedback mechanisms (e.g., buzzer, alarm, siren, LED light, vibrating device) can be included in the torque and/or travel limiter 501. In various embodiments, such other sensory feedback mechanisms can be included with a positive depth stop instead of a torque limiter, can be included with a torque limiter only, or can be included with both a torque limiter and a positive depth stop.

In various embodiments, anchor driver 400 can be used to insert anchor 100 into a bone. In various such embodiments a surgeon can pound tip structure 102 into a bone by pounding on pounding surface 417 with, for example, a mallet or hammer. In various such embodiments, the surgeon or user pounds the tip structure 102 into the bone until the sleeve 101 touches the bone. In such embodiments, continuing to pound on the pounding surface 417 can result in damage to the sleeve 101, referred to as over-insertion damage.

Figure 6B:
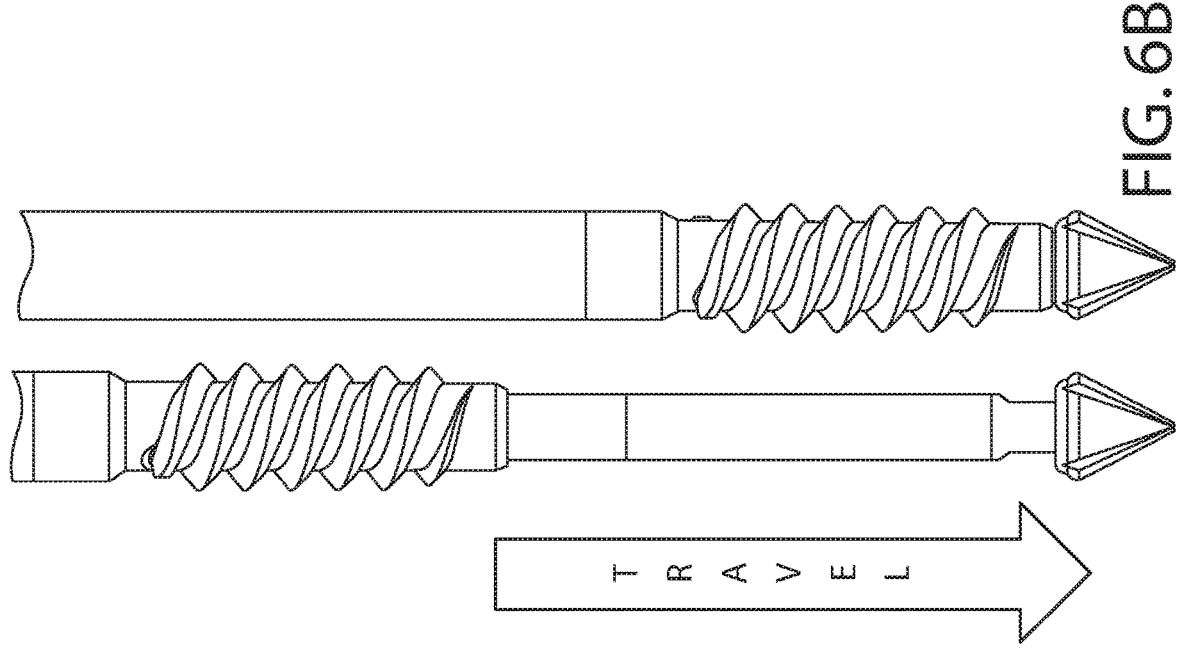
FIGS. 6A-6C are isometric views illustrating a descendable anchor driver in accordance with various embodiments.
Figure 6A:
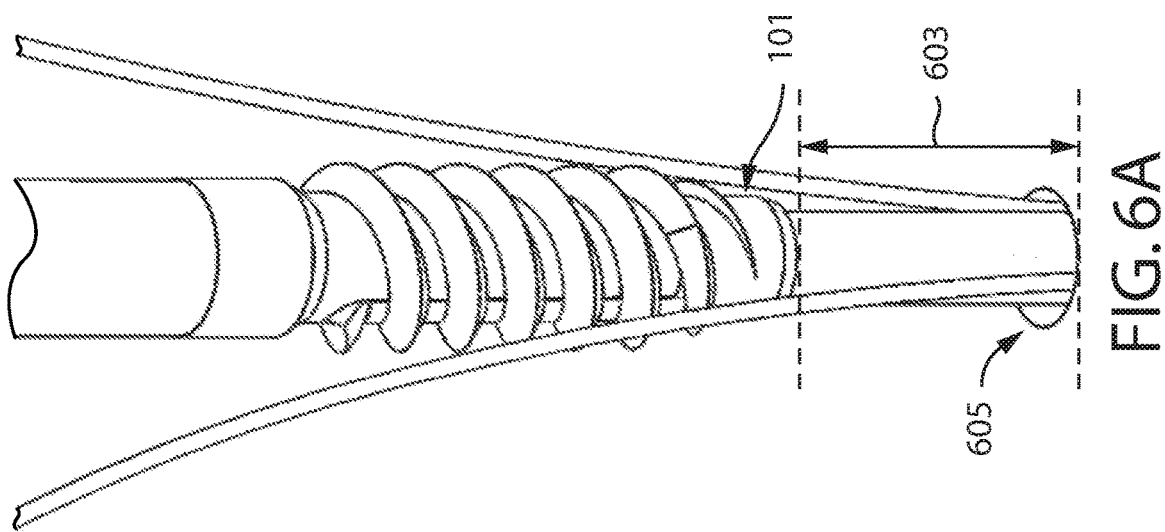
Figure 6C:
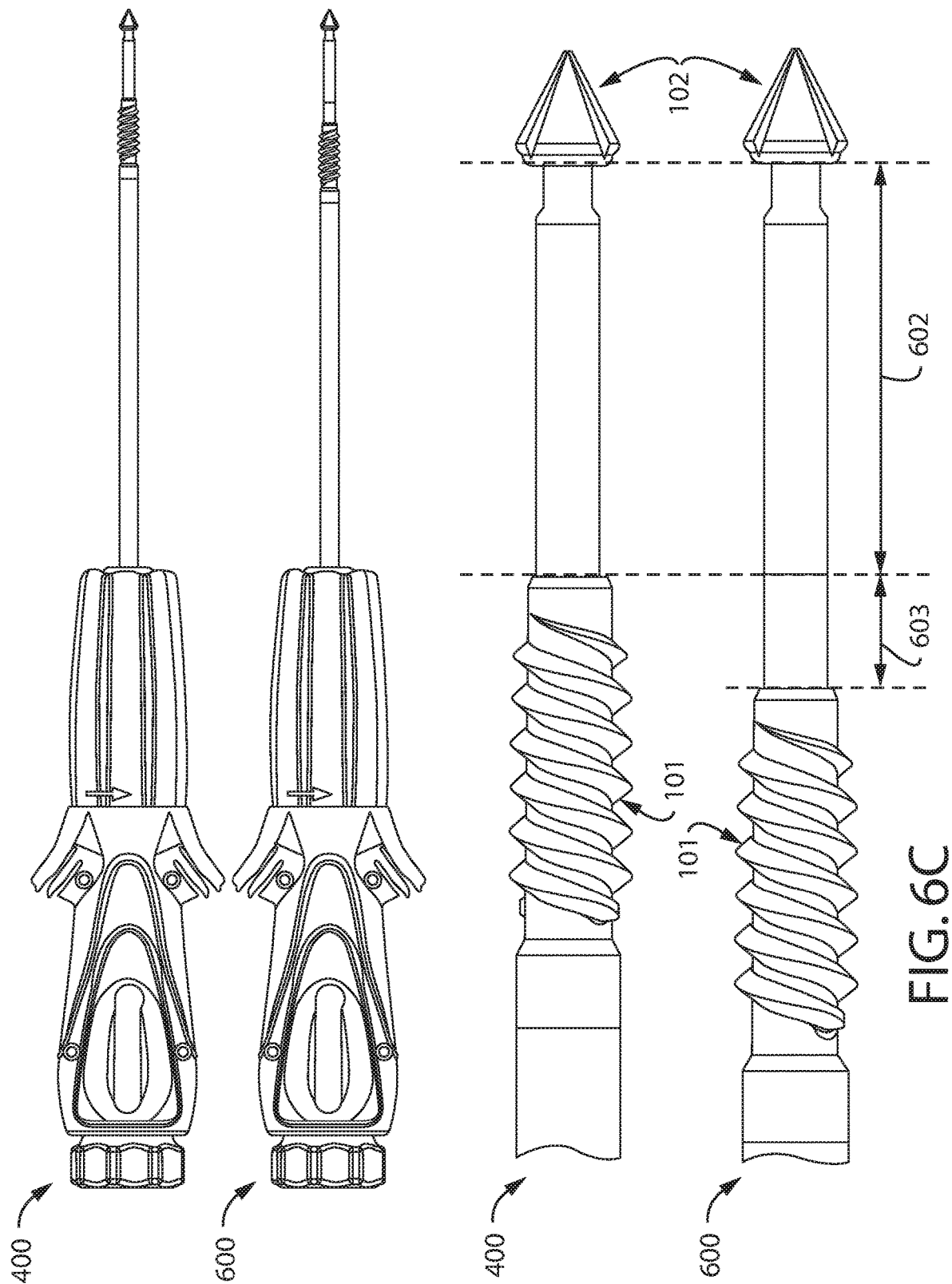

In some example embodiments over-insertion can be avoided, as illustrated in FIGS. 6A-6C, by a descendable anchor driver 600 in accordance with various embodiments. As depicted in FIG. 6A, descendable anchor driver 600 exhibits a nominal clearance 603 between the sleeve 101 and the bone after full insertion of the tip structure 102. As shown in FIGS. 6B and 6C, the nominal clearance 603 can be achieved, for example, by providing an increased clearance between the tip structure 102 and the sleeve 101 when engaged with the descendable anchor driver 600 versus when engaged with the anchor driver 400. In various embodiments, the descendable anchor driver 600 can include a laser mark or other indicator 601 to indicate an appropriate insertion depth 602 of the tip structure 102.

As shown in FIG. 6A, the nominal clearance 603 can, therefore, prevent over-insertion damage to the sleeve 101. As shown in FIGS. 6B and 6C, in various embodiments, the nominal clearance 603 results in an increase in the required longitudinal travel of the outer shaft 601 and sleeve 101 relative to the tip structure 102. In some embodiments, the increased travel is equal to the nominal clearance 603 plus the appropriate tip insertion depth 602.

Figure 7:
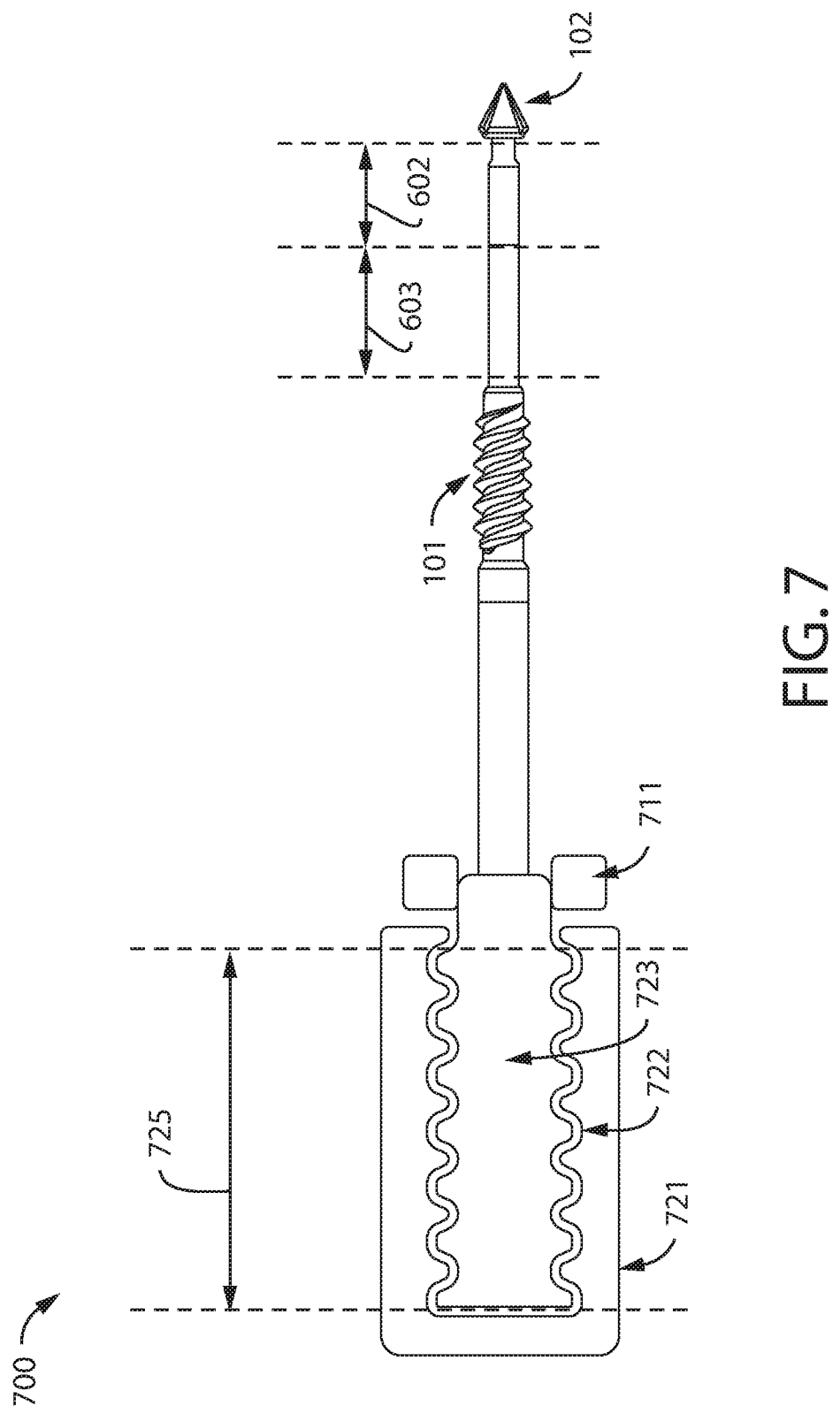
FIG. 7 is cross-sectional view illustrating a descendable anchor driver providing an elongated threaded travel in accordance with various embodiments.

As shown in FIG. 7, a descendable anchor driver 700 in accordance with various embodiments can include an elongated center housing 721, which defines an elongated threaded drive hub receiving cavity 722. The elongated threaded drive hub receiving cavity 722 can be counter-threaded with an elongated outer drive hub 723. In some embodiments, twisting or rotating the sleeve advancement member 711 rotates the elongated outer drive hub 723, thereby causing the elongated outer drive hub 723 to advance distally through the elongated threaded drive hub receiving cavity 722, thereby providing an elongated threaded travel 725 of the sleeve 101. In various embodiments, the elongated threaded travel 725 of the elongated outer drive hub 723 within the elongated threaded drive hub receiving cavity 722 is equivalent to the nominal clearance 603 plus the appropriate tip insertion depth 602. Accordingly, the elongated threaded travel 725 can provide sufficient additional longitudinal travel to compensate for the addition of nominal clearance 603 to anchor driver 600. In various embodiments, elongated center housing 721, elongated threaded drive hub receiving cavity 722, and elongated drive outer drive hub 723 can be, for example, similar to, but longer than, center housing 421, threaded drive hub receiving cavity 422, and outer drive hub 423 respectively.

Figure 8A:
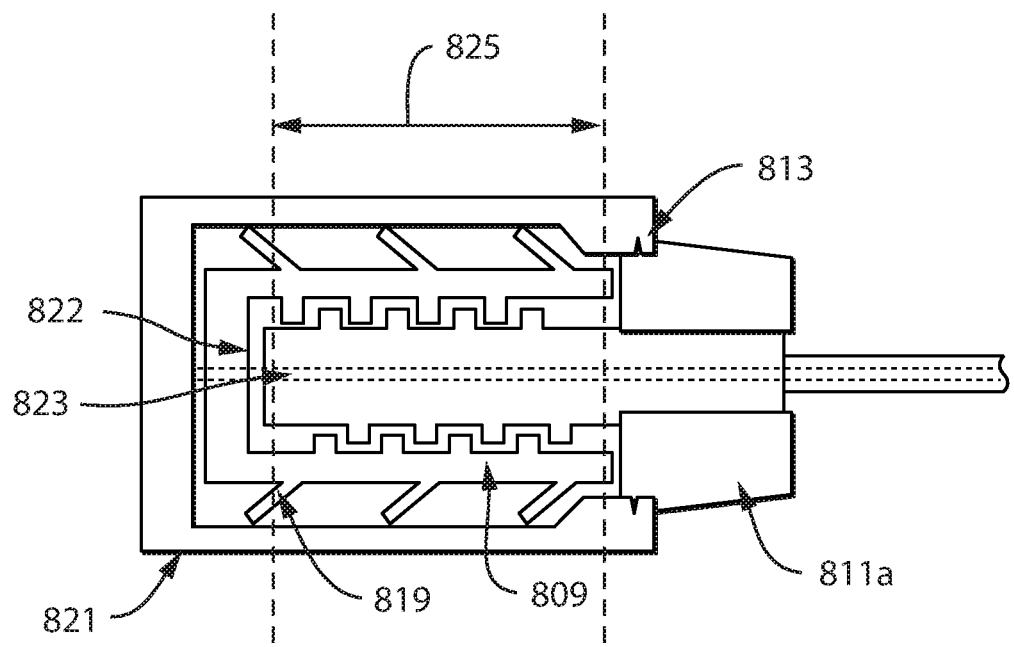
FIGS. 8A-8B are cross-sectional views illustrating a descendable anchor driver having a slidable travel in accordance with various embodiments.
Figure 8B:
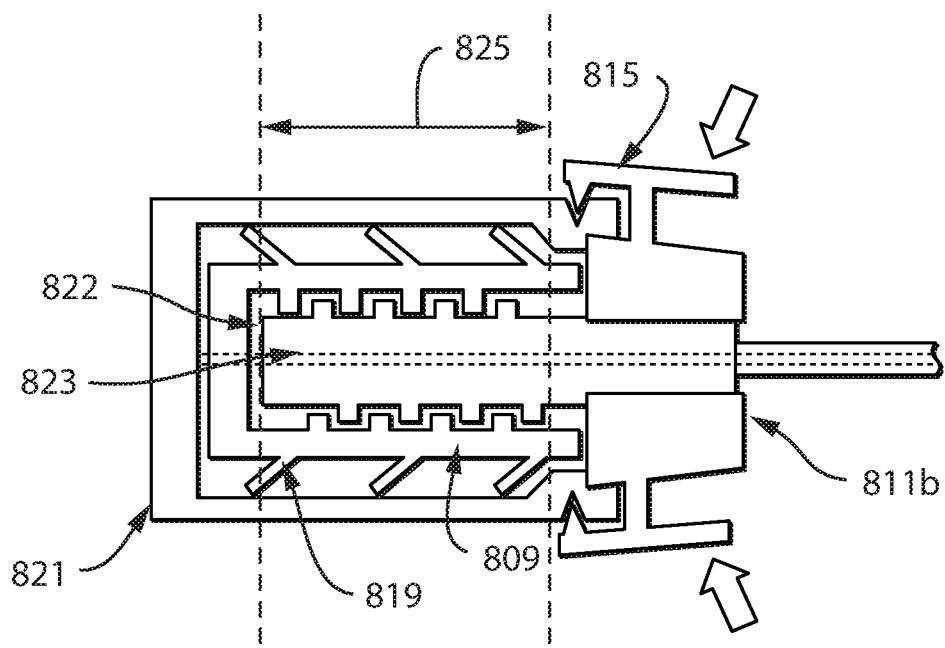

As shown in FIGS. 8A and 8B, a descendable anchor driver 800 can, in various embodiments, include a drive housing 809 positioned within a handle grip 821. The drive housing 809 can define a threaded drive hub receiving cavity 822, which is counter-threaded with an outer drive hub 823. In various embodiments, twisting or rotating the sleeve advancement member 811a, 811b rotates the drive housing 809, thereby causing the outer drive hub 823 to advance distally, thereby providing a threaded travel 825 of the sleeve 101. In some embodiments, threaded drive hub receiving cavity 822 and outer drive hub 823 can be, for example, similar to threaded drive hub receiving cavity 422 and outer drive hub 423.

In various embodiments, the drive housing 809 can be longitudinally slidable within the handle grip 821, thereby providing a slidable travel of the outer shaft 801 relative to the inner shaft 803 to account for the increased travel requirements of a descendable anchor driver (e.g., 600, 700, 800). In various embodiments, a user (e.g., a surgeon) can detach sleeve advancement member 811a, 811b from handle grip 821 in order to slide the drive housing 809 relative to the handle grip 821. Any suitable method of detachment can be used. For example, sleeve advancement member 811a can be detachable via a twisting locking mechanism 813 whereas sleeve advancement member 811b can be detachable via a squeezable locking mechanism 815. In some embodiments, one or more mechanisms (e.g., latches 819) can be used to prevent proximal sliding of the drive housing 809 after advancement, thereby keeping the sleeve suitably close to the bone for screw-in installation. It will be apparent in view of this disclosure that, while radially extending latches 819 are shown, any suitable mechanism can be used to prevent proximal sliding of the drive housing 809 (e.g., a ratchet and/or a braking mechanism).

Figure 9D:
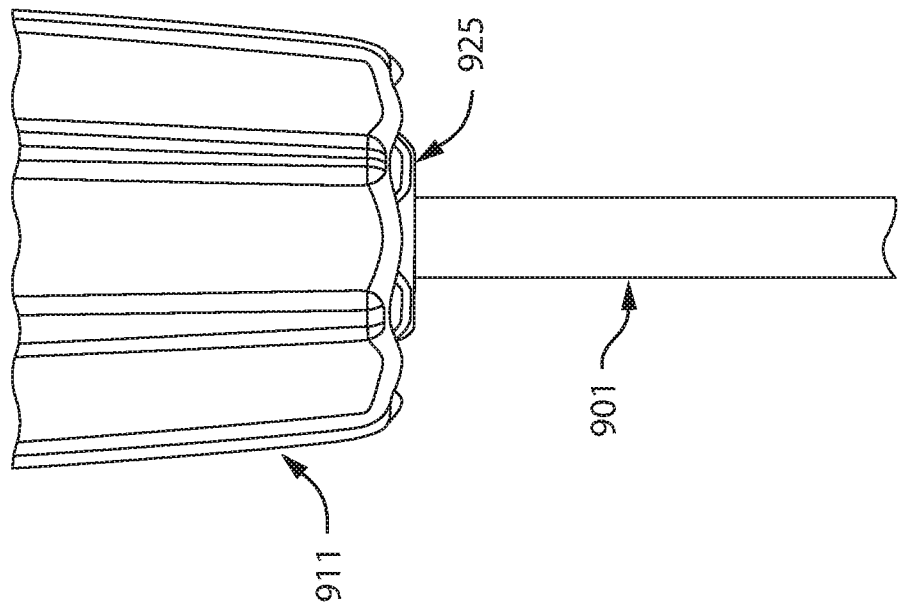

In various embodiments, impact or other axial forces associated with pounding in the tip structure (e.g., 102) which are applied to the sleeve (e.g., 101, 200, 300) can be alleviated to advantageously prevent over-insertion damage. As illustrated by FIGS. 9A-9D, various embodiments can alleviate impact forces by including an axially compliant member 923 (e.g., a spring as shown in FIGS. 9A and 9B) configured to allow a relative motion between the outer shaft 901 and the inner shaft 903, thereby absorbing at least a portion of the impact forces exerted on the sleeve during the pounding-in of the tip structure 102. In some embodiments, the axially compliant member 923 can be positioned between a center housing 921 and a drive housing 909 and be positioned around intermediate shaft 905 and/or inner shaft 903. It will be apparent in view of this disclosure that, while the axially compliant member 923 is depicted to be a compression spring, any suitable axially compliant member 923 can be used. Axially compliant members 923 in accordance with various embodiments can include, for example, a spring, an elastic member, a ratchet mechanism, a hydraulic piston, and/or a pneumatic cylinder.

Figure 9C:
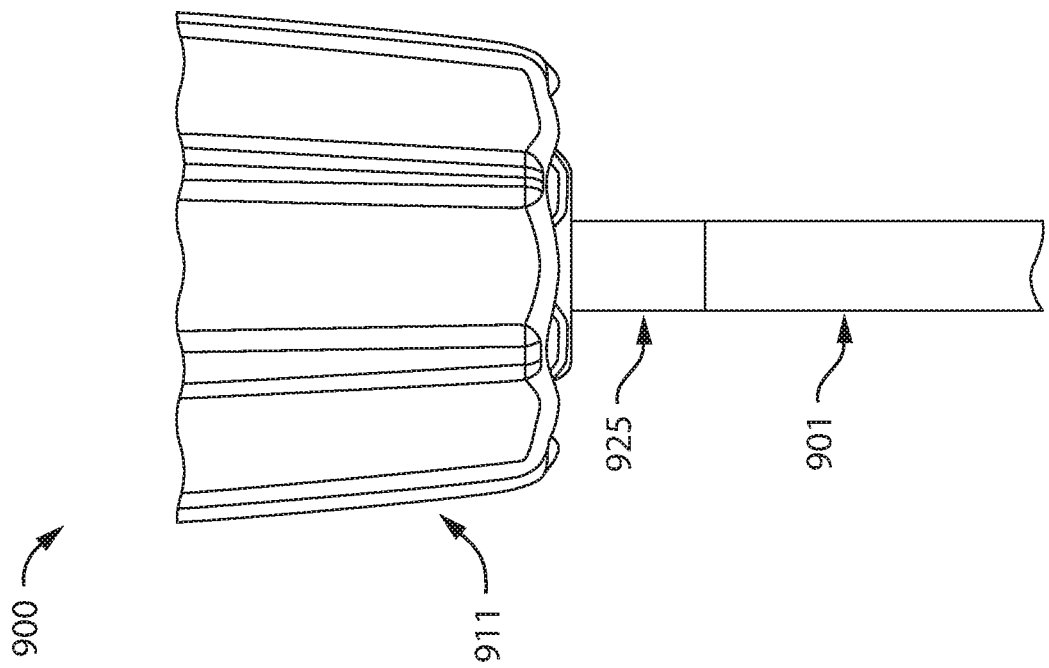
Figure 10C:
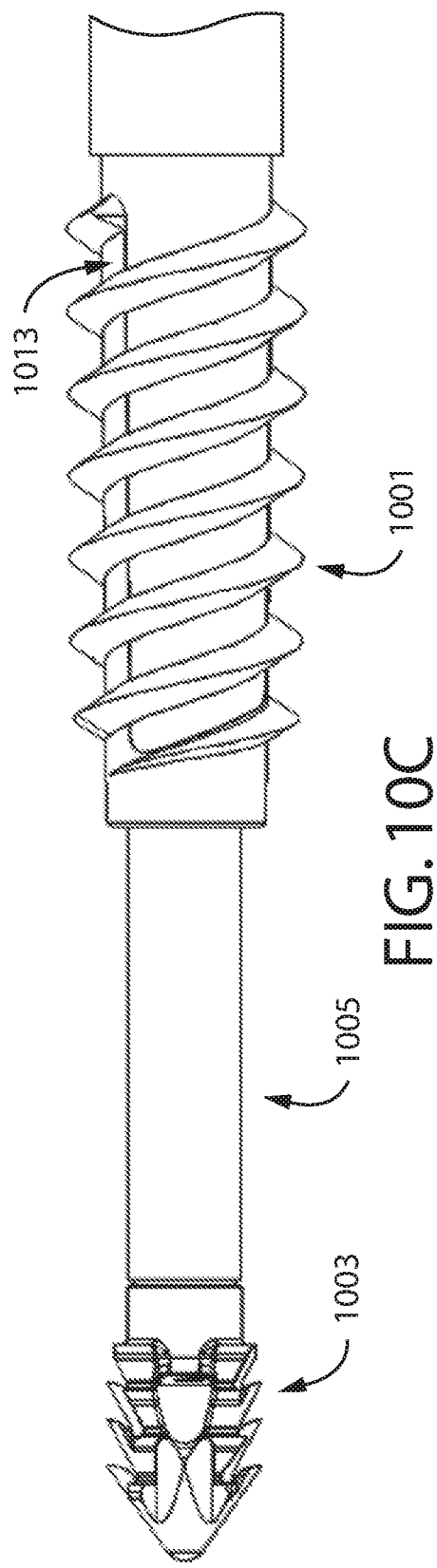
Figure 10D:
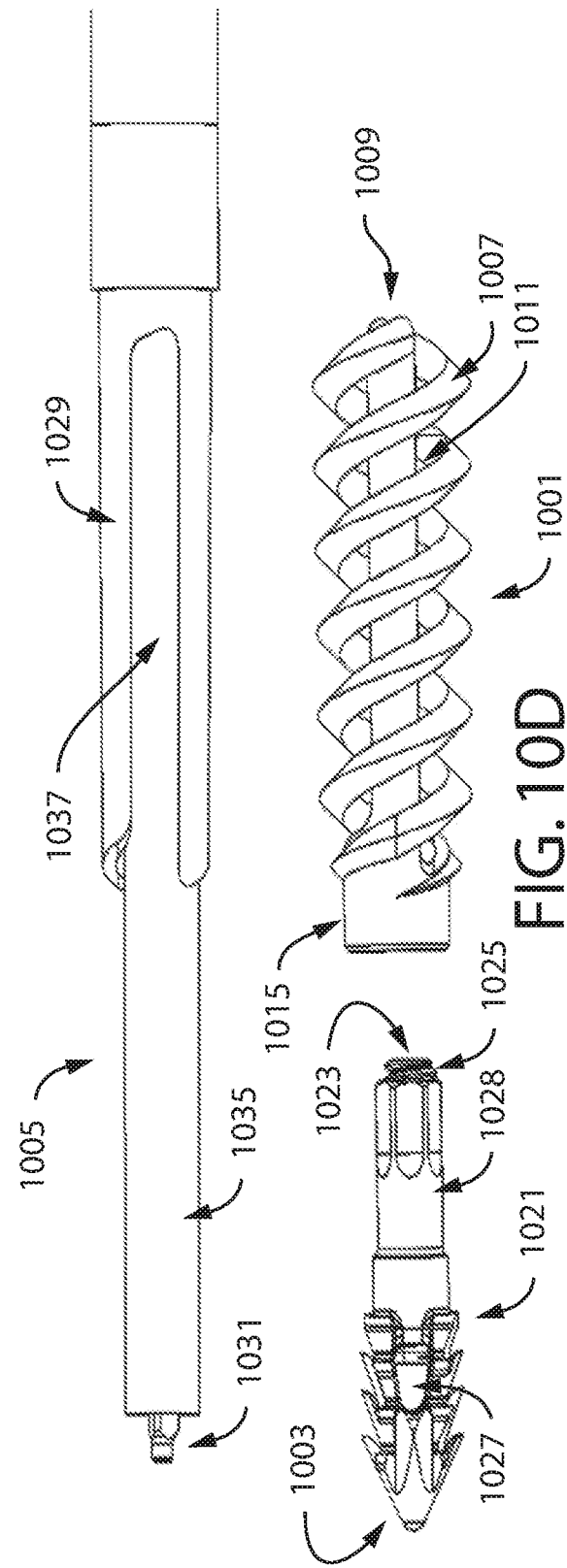

As shown in FIGS. 9C-9D, an anchor driver 900, upon an impact or other axial force being applied to the sleeve 101, provides for the outer shaft 901 to move proximally relative to inner shaft 903. This relative proximal motion of the outer shaft 901 moves the drive housing 909 towards the center housing 921, thereby compressing or otherwise actuating the axially compliant member 923 and absorbing or otherwise relieving the impact forces. In some embodiments, an indicator 925 can be provided along the outer shaft 901 and be retractable into the sleeve advancement member 911. Retraction of the sleeve advancement member 911 can, in various embodiments, alert a user that the tip structure 102 has been fully inserted and that the sleeve 101 is in contact with the bone.

FIGS. 10A-10D illustrate a system for tissue repair 1000 in accordance with various embodiments. The system includes a sleeve 1001 of an anchor, a tip structure 1003 of the anchor, and an anchor driver 1005.

In various embodiments, the sleeve 1001 includes at least one open helical coil 1007, an internal volume 1009 defined within the open helical coil 1007, a plurality of open spacing sections 1011 between turns of the open helical coil 1007, and at least one rib 1013 connected to at least two turns of the open helical coil 1007. The sleeve 1001 can include one or more proximal structural supports (e.g., 203), one or more distal structural supports 1015, and/or one or more circumferential structural supports (e.g., 301). The sleeve 1001 can be similar to, but is not limited to, sleeve 101, 200, 300 described above with reference to FIGS. 1-3 and can be configured to promote bone ingrowth.

In various embodiments, the tip structure 1003 includes a body 1021, an internal cavity 1023 defined within the body 1021, a suture capture member 1025 advanceable through the internal cavity 1023 to capture suture(s) 1026 in an aperture (eyelet) 1027 defined within the body 1021. The tip structure 1003 can also include an intermediate shaft engagement surface 1028 for engaging the intermediate shaft 1035 of the anchor driver 1005. The tip structure 1003 can be similar to, but is not limited to, tip structure 102 described above with reference to FIG. 1. In various embodiments, a suture(s) 1026 can be fed through the aperture 1027 of the tip structure 1003.

In various embodiments, the anchor driver 1005 includes an outer shaft 1029 for holding and advancing the sleeve 1001, an inner shaft 1031 for engaging and advancing the suture capture member 1025, and a handle assembly 1033 for holding and operating the anchor driver 1005. In various embodiments, the anchor driver can also include one or more intermediate shafts 1035 (one as shown) for holding and/or supporting the tip structure 1003. The outer shaft 1029 can define grooves 1037 configured to engage the internal volume 1009 and ribs 1013 of the sleeve 1001. The inner shaft 1031 can be configured to engage the internal cavity 1023 and/or the suture capture member 1025 of the tip structure 1003. The intermediate shaft 1035 can be configured to releasably attach to the intermediate shaft engagement surface 1028 of the tip structure 1003.

The handle assembly 1033 includes a suture capture advancement member (e.g., a knob as shown) 1039 for advancing the suture capture member 1025, a sleeve advancement member (e.g., a collar as shown) 1041 for advancing the sleeve 1001, a handle grip 1043 for holding the anchor driver 1005, one or more suture slots 1045 protruding from the handle grip 1043 for placing and/or maintaining tension on a suture(s) 1026 during installation of the anchor (e.g., sleeve 1001 and tip structure 1003) into bone, a pounding surface 1047 for pounding the tip structure 1003 into bone, and a center housing 1049. The suture capture advancement member 1039 can include a torque and/or travel limiter 1051 for preventing excessive compression of the suture(s) 1026 and breakage of the suture capture member 1025 and/or anchor driver 1005. In some embodiments, the suture capture advancement member 1039 defines a threaded inner shaft receiving cavity 1053, which is counter-threaded with a proximal section of the inner shaft 1031 to allow advancement of the suture capture member 1025. As shown in FIGS. 10A-10D, the center housing 1049 engages with an axially compliant member 1055, which engages with a drive housing 1057 so as to provide absorption of impact and/or other axial forces associated with pounding in the tip structure 1003 which are applied to the sleeve 1001. The drive housing 1057 defines a threaded drive hub receiving cavity 1059, which is counter-threaded with an outer drive hub 1061. The outer drive hub 1061 can be affixed to a proximal end of the outer shaft 1029 and be engaged with the sleeve advancement member 1041, thereby allowing advancement of the sleeve 1001. It will be apparent in view of this disclosure that anchor driver 1005 can be similar to, but is not limited to, any anchor driver 400, 600, 700, 800, 900 described above with reference to FIGS. 4-9.

Figure 11:
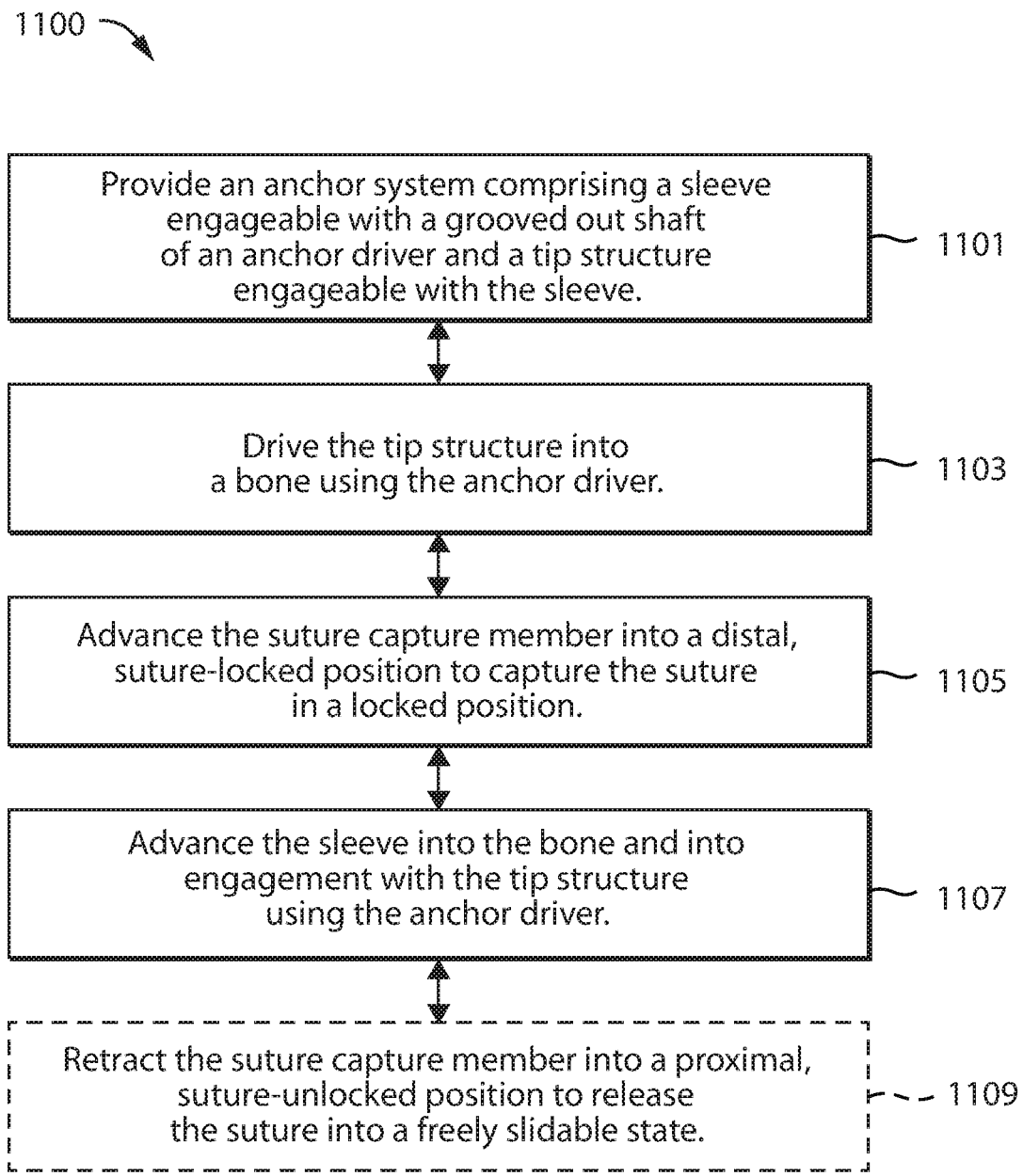
FIG. 11 is a flow chart illustrating a method for tissue repair in accordance with various embodiments.

FIG. 11 illustrates a method for tissue repair 1100 in accordance with various embodiments. The method includes providing an anchor system comprising a sleeve and a tip structure 1101, driving the tip structure into a bone using the anchor driver 1103, advancing the suture capture member into a distal, suture-locked position to capture the suture in a locked position 1105, and advancing the sleeve into the bone and into engagement with the tip structure 1107. In some embodiments, the method for tissue repair 1100 can optionally include retracting the suture capture member into a proximal, suture-unlocked position to release the suture into a freely slidable state 1109.

Providing an anchor system 1101 can, in various embodiments, include providing, for example but not limited to, a system for tissue repair 1000 as described above with reference to FIGS. 10A-10D. It will be apparent in view of this disclosure that any suitable anchor system can be provided in accordance with various embodiments and that such anchor systems can include any anchor and/or anchor driver as described hereinabove with reference to any of FIGS. 1-10.

Driving the tip structure into a bone using the anchor driver 1103 can, in various embodiments, include pounding a pounding surface of the driver to drive the tip structure into the bone. A pounding surface in accordance with various embodiments can be but is not limited to, a pounding surface 417, 1047 as described above with reference to FIGS. 4 and 10.

Advancing the suture capture member into a distal, suture-locked position to capture the suture in a locked position 1105 can, in various embodiments, include twisting or otherwise actuating a suture capture advancement member to advance the inner shaft and, consequently, the suture capture member until a suture is at least partially compressed by the suture capture member within the aperture of the tip structure. A suture capture advancement member in accordance with various embodiments can be but is not limited to, a suture capture advancement member 409, 1039 as described above with reference to FIGS. 4, 5, and 10.

Advancing the sleeve into the bone and into engagement with the tip structure 1107 can, in various embodiments, include twisting or otherwise actuating a sleeve advancement member to advance the outer shaft and, consequently, the sleeve until the sleeve enters the bone and engages with the tip structure. A sleeve advancement member in accordance with various embodiments can be but is not limited to, a sleeve advancement member 411, 711, 811a, 811b, 911, 1041 as described above with reference to FIGS. 4-10.

The optional step of retracting the suture capture member into a proximal, suture-unlocked position to release the suture into a freely slidable state 1109 can, in various embodiments, include twisting or otherwise actuating a suture capture advancement member in a direction opposite of the direction used in the step of advancing the suture capture member 1105 to retract the inner shaft and, consequently, the suture capture member until a suture is at least partially released by the suture capture member within the aperture of the tip structure. A suture capture advancement member in accordance with various embodiments can be but is not limited to, a suture capture advancement member 409, 1039 as described above with reference to FIGS. 4, 5, and 10.

The method of tissue repair 1100 can be used, for example, to perform a tissue repair procedure. The procedure can include drawing a suture(s) 1026 through a soft tissue and placing at least one end of the suture(s) 1026 through the aperture 1027 of the tip structure 1003. In various embodiments, the tip structure 1027 is then pounded into the bone, bringing the sleeve 1001 into a predetermined proximity of the bone (e.g., adjacent to the bone, at a nominal clearance 603 from the bone). The suture capture advancement member 1039, in various embodiments, is then rotated until a feedback mechanism of the torque and/or travel limiter 1051 indicates full advancement. Such rotation serves to advance the suture capture member 1025 into the aperture 1027 to lock the suture(s) 1026 in the aperture 1027.

The sleeve 1001 is then screwed into the bone hole via rotation of the sleeve advancement member 1041, which moves the sleeve 1001 axially and engages the distal end of the sleeve 1001 with the proximal end of the tip structure 1003 and further locks the suture between the sleeve 1001 and the bone. FIG. 10 shows the assembled system for tissue repair with the suture(s) 1026. The suture(s) 1026 can be tensioned prior to advancing the suture capture member 1025 to engage the suture(s) 1026. Optionally, an anchor assembly 100 can be placed within bone, ends of the suture placed through the soft tissue, and the ends then placed through the aperture 107, 1027 of the tip structure 102, 1003. In some embodiments, the suture(s) 1026 can be released by retracting the suture capture member 1025 so that, for example, the user can re-tension the suture 1026. Repair would continue as described above. After tensioning the suture(s) 1026, a user can, in various embodiments, place one or more free ends of the suture(s) 1026 in a suture slot 1045 to help maintain tension during advancement of the suture capture member 1025 into the aperture 1027. A similar type of repair is shown and described in United States Patent Application Publication Nos. 20090112270, 20100016869, and 20100016902, the disclosures of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A system for tissue repair, comprising:
   an anchor comprising:
      a sleeve;
      a tip structure engageable with the sleeve, the tip structure comprising a body defining an internal cavity and an aperture sized to accept a suture, the aperture connected to the internal cavity; and
      a suture capture member advanceable through the internal cavity to capture the suture in the aperture in a locked position; and
   an anchor driver comprising:
      an outer shaft, an outer drive hub coupled to a proximal end of the outer shaft;
      an inner shaft extending through the outer shaft and engageable with the suture capture member; and
   a handle assembly comprising:
      a handle grip for holding the anchor driver;
      a center housing disposed within the handle grip;
      a drive housing disposed within the handle grip distal to the center housing, the drive housing defining a drive hub receiving cavity for threadably receiving the outer drive hub of the outer shaft; and
      an axially compliant member positioned between the center housing and the drive housing, the axially compliant member configured to allow a relative motion between the outer shaft and the inner shaft along a longitudinal axis of the anchor driver.

2. The system of claim 1, wherein the sleeve comprises:
   at least one open helical coil having a proximal end and a distal end, the at least one open helical coil defining an internal volume communicating with a region exterior to the at least one open helical coil through a spacing between turns of the at least one open helical coil; and
   at least one rib disposed within the internal volume, the at least one rib connected to at least two turns of the at least one open helical coil;
   wherein the at least one rib is engageable with corresponding grooves on the outer shaft of the anchor driver.

3. The system of claim 2, wherein the sleeve further comprises one or more proximal structural supports connected to at least two proximal-most turns of the at least one open helical coil.

4. The system of claim 2, wherein the sleeve further comprises one or more distal structural supports connected to at least two distal-most turns of the at least one open helical coil.

5. The system of claim 2, wherein the sleeve further comprises one or more circumferential structural supports disposed between and connected to at least two adjacent turns of the at least one open helical coil.

6. The system of claim 1, wherein the handle assembly further comprises one or more suture slots protruding from the handle grip for placing and/or maintaining tension on the suture during installation of the anchor into bone.

7. The system of claim 1, wherein the handle assembly further comprises a pounding surface for pounding the tip structure into bone.

8. The system of claim 1, wherein the handle assembly further comprises an intermediate shaft positioned between the outer shaft and the inner shaft, the intermediate shaft being releasably attachable to the tip structure.

9. The system of claim 8, wherein the axially complaint member is disposed around one of the inner shaft and the intermediate shaft.

10. The system of claim 1, wherein the handle assembly further comprises a sleeve advancement member operatively coupled to the outer shaft, and wherein rotation of the sleeve advancement member advances the sleeve into engagement with the tip structure.

11. The system of claim 1, wherein a proximal end of the handle assembly comprises a suture capture advancement member operatively coupled to the inner shaft, and wherein rotation of the suture capture advancement member advances the suture capture member into the locked position.

12. The system of claim 11, wherein the suture capture advancement member comprises a torque limiter for limiting a maximum torque applicable to the inner shaft, the torque limiter providing audible feedback to a user.

13. The system of claim 11, wherein the suture capture advancement member comprises a threaded depth stop for limiting a maximum travel of the inner shaft.

14. The system of claim 1, wherein the axially compliant member comprises at least one of a spring, an elastic member, a ratcheting mechanism, or a hydraulic piston.

15. A method of tissue repair comprising:
driving a tip structure of an anchor system into a bone hole with an anchor driver, the anchor system comprising an anchor comprising a sleeve; a tip structure engageable with the sleeve, the tip structure comprising a body defining an internal cavity and an aperture sized to accept a suture, the aperture connected to the internal cavity; and a suture capture member advanceable through the internal cavity to capture the suture in the aperture in a locked position;
advancing, using the anchor driver, the suture capture member to capture the suture in the locked position; and
advancing, using the anchor driver, the sleeve into the bone hole and into engagement with the tip structure;
wherein the anchor driver comprises:
an outer shaft, an outer drive hub coupled to a proximal end of the outer shaft;
an inner shaft extending through the outer shaft and engageable with the suture capture member; and
a handle assembly comprising:
a handle grip for holding the anchor driver;
a center housing disposed within the handle grip;
a drive housing disposed within the handle grip distal to the center housing, the drive housing defining a drive hub receiving cavity for threadably receiving the outer drive hub of the outer shaft; and
an axially compliant member positioned between the center housing and the drive housing, the axially compliant member configured to allow a relative motion between the outer shaft and the inner shaft along a longitudinal axis of the anchor driver.

16. The method of claim 15, further comprising:
engaging at least one rib extending through an internal volume of the sleeve with a corresponding groove on the outer shaft of the anchor driver;
engaging the suture capture member with the inner shaft of the anchor driver; and
releasably attaching the tip structure to an intermediate shaft of the anchor driver positioned between the outer shaft and the inner shaft.

17. The method of claim 15, further comprising exerting a threshold force along the longitudinal axis of the anchor driver causing a retraction of the outer shaft relative to the inner shaft.

18. The method of claim 15, wherein the advancing the sleeve into the bone hole further comprises axially sliding the sleeve along the longitudinal axis of the anchor driver.

19. The method of claim 15, wherein the handle assembly further comprises a sleeve advancement member operatively coupled to the outer shaft, and wherein rotation of the sleeve advancement member causes the advancing the sleeve into the bone hole.

20. The method of claim 15, wherein completing the step of driving the tip structure into the bone hole results in an axial clearance defined along the longitudinal axis of the anchor driver between a surface of the bone hole and a distal end of the sleeve.

* * * * *